(12) United States Patent
Tanaka

(10) Patent No.: US 10,342,507 B2
(45) Date of Patent: Jul. 9, 2019

(54) CONTROL APPARATUS, X-RAY IMAGING SYSTEM, CONTROL SYSTEM, CONTROL METHOD, AND COMPUTER-READABLE MEMORY

(71) Applicant: CANON KABUSHIKI KAISHA, Tokyo (JP)

(72) Inventor: Hikaru Tanaka, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 252 days.

(21) Appl. No.: 14/964,294

(22) Filed: Dec. 9, 2015

(65) Prior Publication Data

US 2016/0166227 A1    Jun. 16, 2016

(30) Foreign Application Priority Data

Dec. 15, 2014  (JP) ................ 2014-253502

(51) Int. Cl.
| | |
|---|---|
| *G06K 9/00* | (2006.01) |
| *A61B 6/00* | (2006.01) |
| *H04L 29/08* | (2006.01) |
| *H04N 1/00* | (2006.01) |
| *H04N 1/21* | (2006.01) |
| *G06F 19/00* | (2018.01) |

(52) U.S. Cl.
CPC ............ *A61B 6/563* (2013.01); *A61B 6/4233* (2013.01); *G06F 19/321* (2013.01); *H04L 67/12* (2013.01); *H04N 1/00095* (2013.01); *H04N 1/2104* (2013.01); *A61B 6/465* (2013.01)

(58) Field of Classification Search
CPC ....... A61B 6/465; A61B 6/563; A61B 6/4233; G06F 19/321; H04L 67/12; H04N 1/00095; H04N 1/2104; G06T 2207/10116; G06T 7/0012
See application file for complete search history.

(56) References Cited

U.S. PATENT DOCUMENTS

| | | | | |
|---|---|---|---|---|
| 2002/0080918 | A1 | 6/2002 | Sako | |
| 2013/0336458 | A1* | 12/2013 | Arima | H05G 1/30 378/98 |
| 2014/0211922 | A1* | 7/2014 | Kuwabara | A61B 6/54 378/97 |
| 2015/0078522 | A1* | 3/2015 | Makino | A61B 6/563 378/62 |
| 2015/0199121 | A1* | 7/2015 | Gulaka | G06F 3/04845 715/771 |

FOREIGN PATENT DOCUMENTS

JP    2016-028628 A    3/2016

* cited by examiner

*Primary Examiner* — Tom Y Lu
(74) *Attorney, Agent, or Firm* — Canon U.S.A., Inc. I.P. Division

(57) ABSTRACT

An imaging control apparatus that controls X-ray imaging includes a controller and a wireless communication circuit that receives an X-ray image and transmits medical information including the X-ray image to a medical imaging archiving system. The controller limits communication of the medical information between the wireless communication circuit and the medical imaging archiving system while the wireless communication circuit is receiving an X-ray image.

21 Claims, 13 Drawing Sheets

FIG. 4

| ITEM | |
|---|---|
| EXAMINATION STATE | NOT CONDUCTED |
| RECEPTION No. | 20140123-0045 |
| SUBJECT ID | 1234-5678 |
| SUBJECT NAME | TARO MARUKO |
| SUBJECT'S DATE OF BIRTH | 6/5/1987 |
| SUBJECT'S GENDER | MALE |
| SUBJECT'S HEIGHT | 175 cm |
| SUBJECT'S WEIGHT | 65 kg |
| PREGNANCY | NO |
| INFECTIOUS DISEASE | NO |
| IMAGE DESTINATION | PACS1, PRINTER2 |
| EXECUTION RESULT INFORMATION DESTINATION | RIS1 |
| IMAGING PROTOCOL ID | 0012, 0013 |

FIG. 5

| ITEM | | |
|---|---|---|
| IMAGING PROTOCOL ID | 0012 | 0013 |
| IMAGING PROTOCOL NAME | FRONT CHEST | SIDE CHEST |
| IMAGING AREA | CHEST | CHEST |
| IMAGING DIRECTION | PA | LR |
| TUBE VOLTAGE | 80 kV | 70 kV |
| TUBE CURRENT | 80 mA | 100 mA |
| RADIATION DURATION | 30 msec | 30 msec |
| GRID ID | 0004 | 0004 |
| OUTPUT SIZE | HALF SIZE | HALF SIZE |

CONTROL APPARATUS, X-RAY IMAGING SYSTEM, CONTROL SYSTEM, CONTROL METHOD, AND COMPUTER-READABLE MEMORY

BACKGROUND

Field

Aspects of the present disclosure generally relate to a control apparatus, an X-ray imaging system, a control system, a control method, and a computer-readable memory that control medical imaging.

Description of the Related Art

An X-ray imaging system has been proposed and used that captures X-ray images using an imaging device such as a digital X-ray sensor and performs image processing on the captured X-ray images. In U.S. Patent Application Publication No. 2002/0080918, an X-ray image subjected to image processing is displayed on a display and checked by a technician. Alternatively, an image might be transmitted from an imaging apparatus to a picture archiving and communication system (PACS) or a network printer and checked by a doctor.

In a control apparatus that controls X-ray imaging, if reception of an image from an imaging device and transmission of an image to a PACS are performed simultaneously, communication delays may occur due to limited capacity of a communication bus or processing performed by a network adapter. Transmission delays of, for example, an image captured by the imaging device, reduce imaging efficiency. Additional delays may occur if unstable wireless communication is performed or a low-performance communication module is used.

SUMMARY

Aspects of the present invention provide a control apparatus that controls an imaging device that obtains an image using a sensor with a plurality of pixels arranged in two dimensions. The control apparatus includes a wireless communication circuit configured to communicate with the imaging device and an external image storage apparatus, a memory configured to store an image transmitted from the imaging device and received by the wireless communication circuit, and a controller configured to limit transmission of the image stored in the memory to the external image storage apparatus while the wireless communication circuit is receiving an image from the imaging device.

Further features of the present disclosure will become apparent from the following description of exemplary embodiments with reference to the attached drawings.

BRIEF DESCRIPTION OF THE DRAWINGS

FIG. 4 is a table illustrating an example of information items included in examination information according to the embodiment.

FIG. 5 is a table illustrating an example of information items included in imaging protocols according to the embodiment.

DESCRIPTION OF THE EMBODIMENTS

Figure 1:
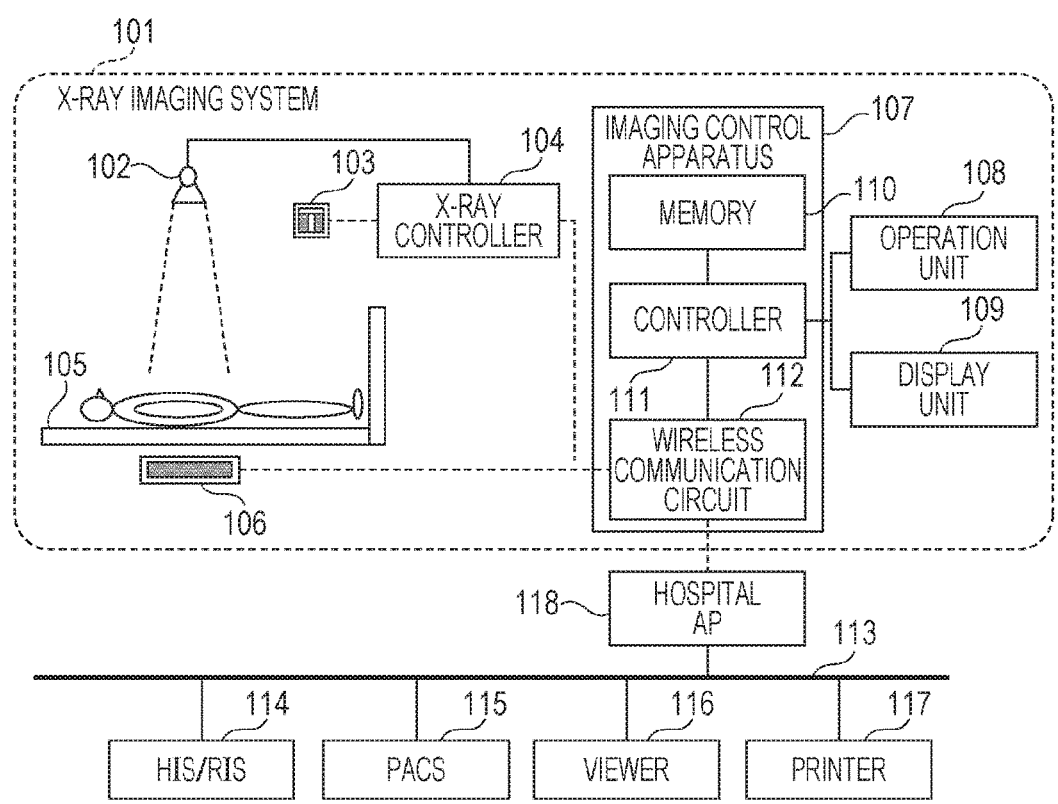
FIG. 1 is a diagram illustrating the configuration of an X-ray imaging system according to an embodiment.

FIG. 1 illustrates the configuration of an X-ray imaging system according to an embodiment. An X-ray imaging system 101 includes an X-ray generation apparatus 102, an X-ray radiation switch 103, an X-ray controller 104, a table 105, an X-ray imaging device 106, an imaging control apparatus 107, an operation unit 108, and a display unit 109. The X-ray imaging system 101 might be referred to as an "X-ray imaging apparatus" while regarding the X-ray generation apparatus 102, the imaging control apparatus 107, and the like as units.

The X-ray imaging system 101 is connected to a hospital information system (HIS)/radiology information system (RIS) 114, a PACS 115, a viewer 116, and a printer 117 at the imaging control apparatus 107 through a network 113. The HIS/RIS 114 is a hospital/radiology department information management system that manages information such as patient information and examination request information in a radiology department. The PACS 115 is an example of an image storage apparatus mainly used for saving images. The viewer 116 is connected to the PACS 115, and a high-definition monitor thereof is mainly used for checking an image captured by the X-ray imaging system 101, performing detailed post-processing on the image, and making a diagnosis. The printer 117 is an apparatus that outputs sheets of paper on which X-ray image data is printed, and is an example of an image storage apparatus according to an embodiment in that the printer 117 receives an image and is used for at least temporarily storing the image.

The X-ray generation apparatus 102 begins to radiate X-rays and stops radiating the X-rays. The X-ray generation apparatus 102 also transmits imaging conditions such as tube voltage and tube current to the X-ray controller 104 in accordance with radiation of X-rays. The X-ray generation apparatus 102 receives default imaging conditions from the X-ray controller 104 and performs a process for preparing for imaging. The X-ray radiation switch 103 transmits a radiation start notification or a radiation end notification to the X-ray controller 104. If pressed by an operator, the X-ray radiation switch 103 transmits a radiation start notification. If released by the operator, the X-ray radiation switch 103 transmits a radiation end notification. The X-ray controller 104 is connected to the X-ray generation apparatus 102, the X-ray radiation switch 103, and the imaging control apparatus 107. The X-ray controller 104 controls a start and an end of radiation of X-rays and transmits imaging conditions. The X-ray controller 104 receives default imaging conditions from the imaging control apparatus 107 and transmits the default imaging conditions to the X-ray generation apparatus 102. The table 105 is a platform on which a subject is placed.

The X-ray imaging device 106 is an example of a sensor unit for capturing a medical image. The X-ray imaging device 106 includes a sensor array in which a plurality of pixels are arranged in two dimensions, a communication circuit that outputs an image obtained from the sensor array to the imaging control apparatus 107, and an arithmetic processing circuit that integrally controls the operation of the sensor array. In one embodiment, the pixels included in the sensor array are composed of amorphous selenium (a-Se) that converts X-rays into electric signals and electrodes. In one embodiment, the a-Se and an upper electrode are shared by the plurality of pixels, and a plurality of lower electrodes that collect charges are arranged in a matrix with gaps provided therebetween. Each lower electrode corresponds to one pixel. In another embodiment, the sensor array includes a scintillator composed of CsI(Tl) or the like that converts X-rays into visible light. Photoelectric conversion elements with sensitivity to visible light convert the visible light obtained as a result of the conversion from the X-rays performed by the scintillator into electric signals. In this case, each photoelectric conversion element corresponds to one pixel. Each pixel includes the photoelectric conversion element and a switching element for outputting an electric signal of the photoelectric conversion element. A common row selection line is connected to a base of the switching element in a row direction. The photoelectric conversion element is connected to either a collector or an emitter of the switching element, and a common column signal line is connected to the other of the collector and the emitter in a column direction. The row selection lines are connected to a driving circuit including a shift register, and voltages V1 and V2 (>V1) for turning on and off the switching devices are applied to the row selection lines. An accumulation state, in which electric signals are accumulated in the pixels, is established by turning off the switching devices, and an output state, in which electric signals are output, is established by turning on the switching devices. One end of each photoelectric conversion element is connected to the corresponding switching device, and another end is connected to a bias supply. The column signal lines are connected to a reading circuit that includes an amplifier and an analog-to-digital (A/D) converter. The driving circuit sequentially outputs electric signals from the pixels, and the reading circuit converts the output electric signals into digital signals to obtain digital X-ray image data. The driving circuit, the reading circuit, and the bias supply are connected to the arithmetic processing circuit in the X-ray imaging device 106. The arithmetic processing circuit controls the accumulation state and the output state of the sensor array, a process for reading electric signals output from the sensor array, and an application state of bias voltage to the sensor array.

The X-ray imaging device 106 converts X-rays that have passed through the subject into X-ray image data to obtain a two-dimensional X-ray image. The X-ray imaging device 106 is connected to the imaging control apparatus 107 and transmits the X-ray image data obtained as a result of the conversion to the imaging control apparatus 107 along with imaging execution result information such as a reading area and a binning size. The transmission of X-ray image data and imaging execution result information is performed through wired communication in which a cable connected to the imaging control apparatus 107 is used or wireless communication.

The imaging control apparatus 107 is a control apparatus that controls imaging performed by the X-ray imaging device 106. The imaging control apparatus 107 controls X-ray imaging in combination with the X-ray controller 104 and the X-ray imaging device 106, image processing for X-ray image data, such as tone processing, execution of examinations including X-ray imaging, input and output of the operation unit 108 and the display unit 109, and communication with external apparatuses through the network 113. The imaging control apparatus 107 includes a memory 110, a controller 111, and a wireless communication circuit 112.

The wireless communication circuit 112 transmits an X-ray radiation preparation request or an X-ray radiation preparation cancellation request to the X-ray controller 104 and the X-ray imaging device 106 through a communication interface. The wireless communication circuit 112 receives X-ray image data and imaging information from the X-ray controller 104 and the X-ray imaging device 106. The wireless communication circuit 112 receives examination request information, transmits examination execution result information, and outputs X-ray image data through the network 113.

The wireless communication circuit 112 of the imaging control apparatus 107 wirelessly communicates with the X-ray imaging device 106. The wireless communication circuit 112 may wirelessly communicate with the X-ray controller 104, too. Alternatively, the X-ray imaging device 106 need not communicate with the wireless communication circuit 112 using a wireless communication module but an external wireless communication module connected to the X-ray imaging device 106 by wire may communicate with the wireless communication circuit 112 of the imaging control apparatus 107.

The wireless communication circuit 112 can communicate with apparatuses connected to the hospital network 113, such as the PACS 115, by wirelessly communicating with a hospital access point (AP; or a communication base station) 118.

The memory 110 is used for storing an image based on an image transmitted from the X-ray imaging device 106 and received by the wireless communication circuit 112. The received image may be stored, or an image obtained by performing a high-definition process, such as a noise reduction process, on the received image may be stored.

The controller 111 performs control relating to examinations and imaging, saves and reads examination execution result information and X-ray image data, and controls output of images. The controller 111 exclusively performs reception of an image from the X-ray imaging device 106 and transmission of an image to the PACS 115 using the wireless communication circuit 112. In order to give priority to the imaging over the transmission of an image to the PACS 115, for example, the controller 111 limits the transmission of an image stored in the memory 110 to the wireless communication circuit 112 while the wireless communication circuit 112 is receiving an image from the X-ray imaging device 106. The controller 111 controls the wireless communication circuit 112, for example, such that the wireless communication circuit 112 does not transmit an image stored in the memory 110. The possibility of a communication delay due to an insufficient communication band used by the wireless communication circuit 112 can thus be reduced.

On the other hand, if a communication cable is connected to the imaging control apparatus 107, the controller 111 causes the wireless communication circuit 112 to transmit an image stored in the memory 110 to the PACS 115 through the communication cable even while the wireless communication circuit 112 is receiving an image. In this case, the imaging control apparatus 107 includes a connector for connecting a cable to the X-ray imaging device 106, and the arithmetic processing circuit integrally controls the transmission regardless of whether a cable is used.

In doing so, the possibility of a communication delay can be reduced, and X-ray imaging can be efficiently performed.

On the other hand, in the case of communication in which the amount of data transmitted is small and its communication load does not affect the whole communication process, no limitation needs to be put on. In one embodiment, the controller 111 limits the transmission of an image stored in the memory 110 to the PACS 115 while the wireless communication circuit 112 is receiving an image from the X-ray imaging device 106, but the wireless communication circuit 112 can receive an imaging order from the HIS/RIS 114 and transmit imaging execution result information to the HIS/RIS 114. The imaging order herein refers to imaging request information including imaging conditions such as an imaging area and an imaging direction, and the imaging execution result information herein refers to information including a dose used for imaging and radiation conditions. In doing so, the limitation of communication can be minimized in order not to affect the whole communication process.

The operation unit 108 is an input interface that receives an operation performed by the operator. The operation unit 108 may be a keyboard, a mouse, a multi-touch monitor, or any other input interface. The operation unit 108 transmits input information to the imaging control apparatus 107 in accordance with an operation performed by the operator. The operation unit 108 also receives a request from the imaging control apparatus 107 to switch content displayed thereon. The display unit 109 is an output interface that displays a user interface of control software for X-ray imaging. The display unit 109 may be an independent monitor, a monitor incorporated into the X-ray imaging system 101, or any other interface that can display content. A plurality of monitors that display captured images might be connected to the imaging control apparatus 107, and a captured image and a past image might be displayed on different monitors as previews. In this case, the display unit 109 determines which monitor displays which image in accordance with a notification from the imaging control apparatus 107 and displays the images. A touch panel monitor, which can serve as the display unit 109 into which a touch panel as the operation unit 108 is incorporated, may be used, instead.

Figure 2:
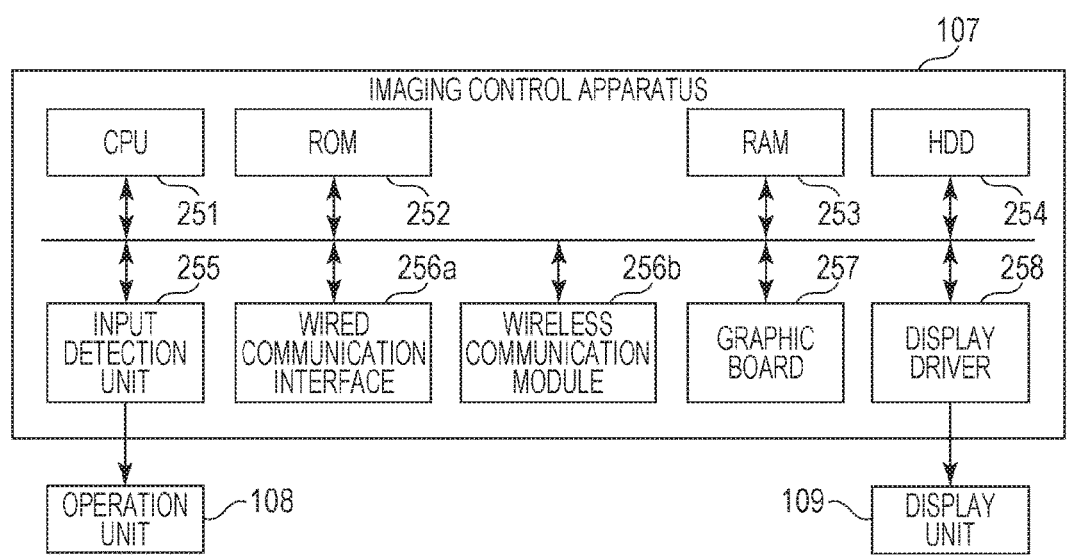
FIG. 2 is a diagram illustrating the hardware configuration of an imaging control apparatus according to the embodiment.

Next, FIG. 2 illustrates the hardware configuration of the imaging control apparatus 107 according to the present embodiment. The controller 111 includes a central processing unit (CPU) 251, a read-only memory (ROM) 252, a random-access memory (RAM) 253, a hard disk drive (HDD) 254, an input detection unit 255, a wired communication interface 256a, a wireless communication module 256b, a graphic board 257, and a display driver 258. These components are connected to one another through a bus such as a data bus. The CPU 251 is an arithmetic processing circuit that controls the entirety of the controller 111 and realizes control according to the present embodiment by executing commands included in a program, which is loaded into the RAM 253, for performing processes illustrated in flowcharts of FIGS. 6, 7, 8, 9, and 10, which will be referred to later. The CPU 251 also performs output control for the display unit 109 through the display driver 258 and input control for the operation unit 108 through the input detection unit 255. The RAM 253 secures a working storage when the CPU 251 performs control according to a command program. The HDD 254 is a memory that saves various pieces of data such as X-ray image data. The wired communication interface 256a is a communication module including a connector for a communication cable. The wireless communication module 256b is a communication module that performs wireless communication and communicates data between the controller 111 and the X-ray imaging device 106, the hospital AP 118, or the X-ray controller 104. The graphic board 257 outputs, to the display unit 109, image data obtained through image processing performed by a graphics processing unit (GPU).

The wireless communication module 256b corresponds to the wireless communication circuit 112, the HDD 254 corresponds to the memory 110, and the CPU 251 corresponds to the controller 111.

In one embodiment, functions realized by the software program may be realized by hardware such as a field-programmable gate array (FPGA). The software program may be converted into configuration information for the FPGA, and the functions may be realized by the FPGA. In this case, the FPGA may be configured such that hardware blocks corresponding to function blocks illustrated in FIG. 3, which will be referred to hereinafter, are provided.

Figure 3:
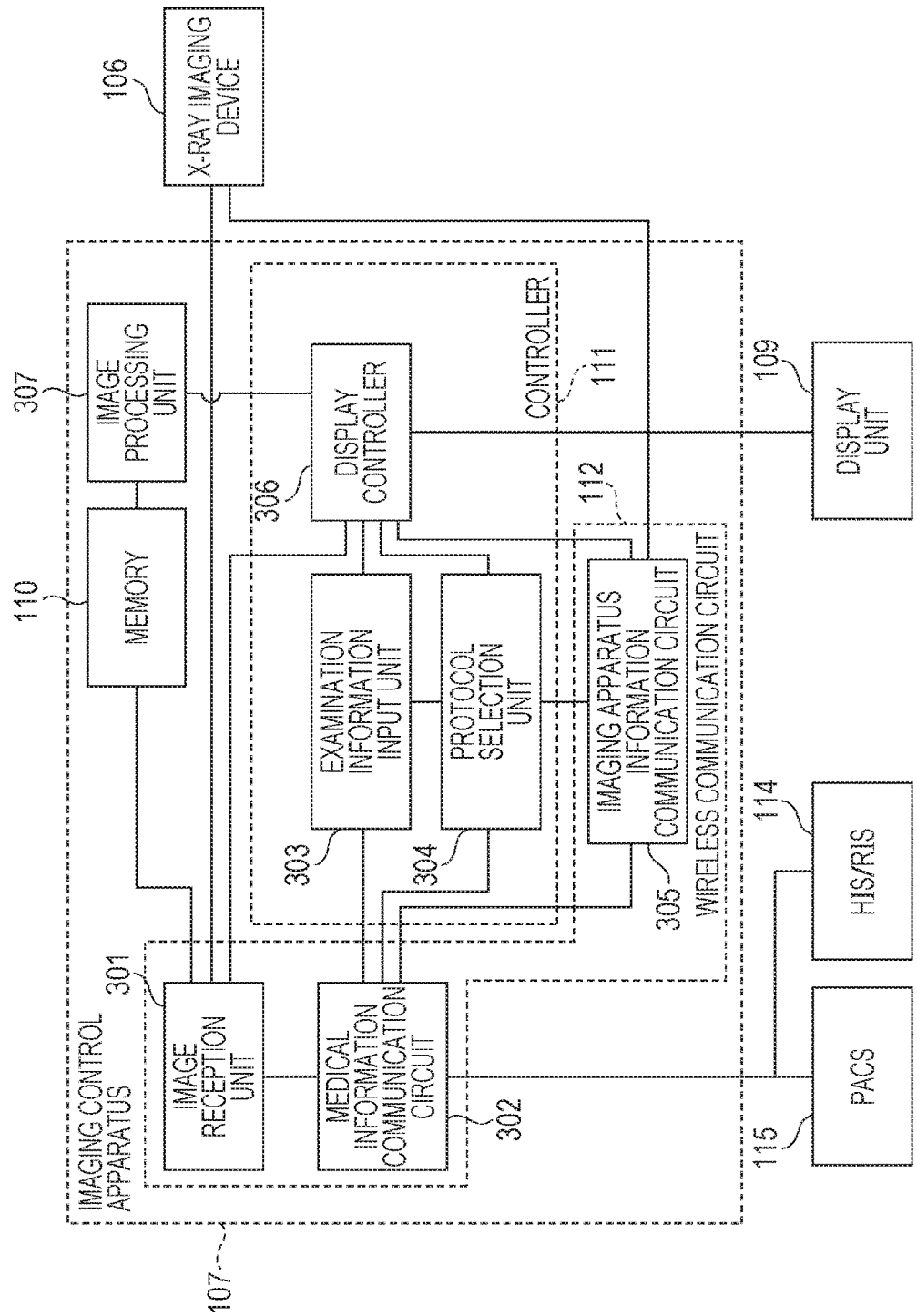
FIG. 3 is a diagram illustrating a relationship between functions realized by the imaging control apparatus according to the embodiment.

A relationship between functions realized by the imaging control apparatus 107 will be described with reference to FIG. 3. The following functions are realized, for example, by the hardware illustrated in FIGS. 1 and 2 and the above-described software program.

The imaging control apparatus 107 includes the memory 110, an image reception unit 301, a medical information communication circuit 302, an examination information input unit 303, a protocol selection unit 304, an imaging apparatus information communication circuit 305, a display controller 306, and an image processing unit 307. The image reception unit 301, the medical information communication circuit 302, and the imaging apparatus information communication circuit 305 correspond to the wireless communication circuit 112, and the examination information input unit 303, the protocol selection unit 304, and the display controller 306 correspond to the controller 111.

The image reception unit 301 receives an X-ray image from the X-ray imaging device 106. The medical information communication circuit 302 communicates with servers that manage medical information, such as the PACS 115 and the HIS/RIS 114.

The imaging apparatus information communication circuit 305 obtains information including information regarding the temperature and a battery of the X-ray imaging device 106 included in examination information, sets imaging conditions including a driving mode of the X-ray imaging device 106, and performs state control such as shifting of the X-ray imaging device 106 to an imaging available state.

The image reception unit 301 and the X-ray imaging device 106 may communicate with each other through a cable or wirelessly. If the image reception unit 301 and the X-ray imaging device 106 wirelessly communicate with each other, either the image reception unit 301 or the X-ray imaging device 106 may function as an access point. Similarly, the medical information communication circuit 302 and the PACS 115 or the HIS/RIS 114 may communicate with each other through a cable or wirelessly. If the medical information communication circuit 302 and the PACS 115 or the HIS/RIS 114 wirelessly communicate with each other, either the medical information communication circuit 302 or the PACS 115 or the HIS/RIS 114 may function as an access point.

The examination information input unit 303 obtains examination information through manual input by the operator or through the HIS/RIS 114. The examination information includes information regarding a subject and imaging information such as an imaging area corresponding to at least one X-ray imaging operation. The protocol selection unit 304 selects an imaging protocol including an imaging area and an X-ray radiation direction in the imaging area used for X-ray imaging. The imaging protocol is information corresponding to one piece of imaging information included in the examination information and includes processing conditions for one imaging operation, such as imaging conditions including an imaging area, an imaging direction, an imaging method, radiation conditions, and the driving mode of the X-ray imaging device 106, image processing conditions, and image output conditions. Details of the examination information and the imaging protocol will be described later with reference to FIGS. 4 and 5.

The display controller 306 displays, on the display unit 109, an image based on an X-ray image received by the image reception unit 301 and graphical user interfaces (GUIs) for allowing the operator to input commands. Examples of the GUIs will be described with reference to FIGS. 11 and 12.

The image processing unit 307 processes an X-ray image obtained from the X-ray imaging device 106. The image processing unit 307 performs a property correction process including dark correction, gain correction, and defective pixel correction necessitated by properties of the sensor, a noise reduction process including a line noise correction process and a scattered radiation correction process, a high-definition process including a tone conversion process and a sharpening process, and the like. An image to which at least part of these processes, such as the property correction process, has been applied may be stored in the memory 110, and image processing parameters of the noise reduction process and the high-definition process may be associated with the image as additional information regarding the image and stored in the memory 110.

The controller 111 integrally controls the operation of the imaging control apparatus 107.

An example of items and values included in the examination information will be described with reference to a table of FIG. 4. Examination state is an item that manages whether the examination has not been conducted, has already started (being conducted), or has been completed. Before the examination, "not conducted" is displayed. After the start of the examination, "started" is displayed. After the end of the examination, "completed" is displayed. Reception No. is identification (ID) information regarding the examination. Subject ID is an ID of the examination information. The subject ID, subject name, subject's date of birth, subject's gender, subject's height, subject's weight, pregnancy, and infectious disease are information regarding a subject. The subject ID is a unique value give to each subject.

Image destination is information indicating a destination of an X-ray image obtained as a result of the examination (X-ray imaging) and, in the example illustrated in FIG. 4, expressed as identifiers of image storage apparatuses, such as PACS1 and PRINTER2. A private Internet Protocol (IP) address that identifies a destination of data, for example, is associated with each of the identifiers, and the X-ray image is transmitted to the destination in practice. Execution result information destination is information indicating a destination of execution result information. The execution result information is information indicating a destination of an examination state, radiation conditions used for X-ray imaging, and information indicating a radiation dose for the subject used in the X-ray imaging. In the example illustrated in FIG. 4, RIS1, which is an identifier of the destination, is indicated. A private IP address that identifies a destination of data is associated with the identifier, too, and the execution result information is transmitted to the destination.

Imaging protocol ID is identification information regarding an imaging protocol, which is a series of processing conditions relating to X-ray imaging. The imaging protocol ID included in the examination information is information regarding an imaging order, and imaging corresponding to the imaging protocol ID is performed. In the example illustrated in FIG. 4, two imaging operations, namely 0012 and 0013, are requested in one examination.

An example of items and values included in an imaging protocol will be described with reference to a table of FIG. 5. As described above, the imaging protocol ID is identification information for identifying the imaging protocol, which indicates the processing conditions. Imaging protocol name is information displayed in an imaging screen (FIG. 12), which will be described later, for example, when information corresponding to the imaging protocol is displayed. Imaging area is information indicating a body part to be subjected to imaging. Imaging direction is information indicating an X-ray radiation direction for the subject. Imaging method is information indicating an imaging method such as a still image, fluoroscopy, digital subtraction angiography (DSA), or tomography. Tube current, tube voltage, and radiation duration are information indicating X-ray radiation conditions set for the X-ray generation apparatus 102. Grid ID is information for identifying the type of grid and includes information such as a grid ratio, grid density, shape information regarding the grid such as parallel grid, focused grid, or cross grid, and an operation method of the grid, such as moving grid or still grid. If a grid is not used, information such as "0000", for example, is used.

Output size is information that identifies the output size of an X-ray image obtained as a result of imaging. In the example illustrated in FIG. 5, half size is used in both first and second protocols.

A control flow according to an embodiment will be described with reference to the flowchart of FIG. 6.

In step S101, the examination information input unit 303 obtains input examination information. The examination information may be input, for example, through an operation in which a GUI displayed by the display controller 306 on the display unit 109 is used (FIG. 11) or from the examination information from the HIS/RIS 114 through the medical information communication circuit 302.

In step S102, the controller 111 starts an examination based on the examination information input in step S101. After the examination starts, the information regarding the examination state included in the examination information changes from "not conducted" to "started". The examination may be started by the operator using a GUI displayed on the display controller 306 or may be automatically started in accordance with the input of the examination information. After the examination starts, for example, the display controller 306 may display the imaging screen (FIG. 12) on the display unit 109.

In step S103, the controller 111 determines whether the examination is to be ended. The examination is ended, for example, through an operation in which a GUI displayed on the display controller 306 is used (FIG. 12) or after all imaging operations of imaging protocols end. If the examination is to be ended, the process proceeds to step S101. If the examination is not to be ended, the process proceeds to step S104.

In step S104, the protocol selection unit 304 selects an imaging protocol used for X-ray imaging from among imaging protocols associated with the examination information input in step S101. The imaging protocol may be selected by the operator using a GUI displayed on the display controller 306 (FIG. 12) or may be automatically selected in accordance with the start of the examination. If two imaging protocols are associated with the examination information regarding the examination that has started, for example, the protocol selection unit 304 selects an imaging protocol in accordance with an input operation or a certain rule.

In step S105, the controller 111 causes the imaging apparatus information communication circuit 305 to output, to the X-ray imaging device 106, a signal for shifting the X-ray imaging device 106 to the imaging available state.

If a plurality of X-ray imaging devices 106 are communicably connected to the imaging control apparatus 107, the controller 111 outputs a signal for shifting one of the X-ray imaging devices 106 determined on the basis of the imaging protocol to the imaging available state. If an imaging protocol for a front abdomen, for which imaging is performed with a subject laid down, is selected with a first X-ray imaging device held by a holding unit provided for the table 105 and a second X-ray imaging device inserted into a standing imaging table, for example, the controller 111 outputs a signal for shifting the first X-ray imaging device, which corresponds to the imaging protocol, to the imaging available state. The imaging available state refers to a state in which the properties of the sensor array of the X-ray imaging device 106 are stable. In order to establish the imaging available state, if bias voltage is not applied to the sensor array, the X-ray imaging device 106 applies the bias voltage to the sensor array. The X-ray imaging device 106 repeats an operation for establishing the output state and the accumulation state for all the pixels several times to complete initialization, in which outputs of the pixels stabilize. In the imaging available state, the sensor array of the X-ray imaging device 106 repeats an idle reading operation, in which the output state and the accumulation state are established for all the pixels.

If the imaging area is an abdomen, X-ray radiation duration is longer than when the imaging area is a chest or the like. In this case, the controller 111 also outputs a signal for changing the accumulation time of the X-ray imaging device 106 from default 1 second to 3 seconds.

If the imaging control apparatus 107 and the X-ray controller 104 are communicably connected to each other through a cable or wirelessly, the imaging apparatus information communication circuit 305 transmits the X-ray radiation conditions included in the imaging protocol to the X-ray controller 104 in accordance with the selection performed by the protocol selection unit 304.

In step S106, the controller 111 determines whether there has been an instruction to cancel the selection of an imaging protocol, such as a change to an imaging protocol to be used for imaging or a temporary stop of the imaging. The selection of an imaging protocol may be canceled by the operator using a GUI displayed on the display controller 306 (FIG. 12), on the basis of detection of an event such as an error inside the imaging control apparatus 107, or on the basis of a notification from the X-ray imaging device 106. If the selection of an imaging protocol is to be canceled, the process proceeds to step S114. If the selection of the imaging process is not to be canceled, the process proceeds to step S1071.

In step S114, the controller 111 causes the imaging apparatus information communication circuit 305 to transmit a signal for shifting the X-ray imaging device 106 to an imaging unavailable state. The imaging unavailable state refers to a state in which even if the X-ray imaging device 106 receives a signal for requesting permission for X-ray radiation, the X-ray imaging device 106 is not allowed to perform X-ray radiation, that is, for example, a state in which the bias voltage is not applied to the sensor array or a state in which an initialization process is being performed. The imaging unavailable state also includes a state in which the sensor array can perform imaging but a memory state flag of the X-ray imaging device 106 indicates the "imaging unavailable state". It is therefore possible to prevent imaging in a state in which an imaging protocol is not selected and resultant unknown association between an X-ray image and imaging information.

In step S115, the protocol selection unit 304 cancels the selection of an imaging protocol. In one embodiment, in order to manage the selection (or lack thereof) of an imaging protocol, the imaging protocol includes state information indicating "not selected", "selected", "imaging complete", "image processing completed", or "output". The controller 111 updates the state information included in the imaging protocol in accordance with a notification indicating selection or cancelation of selection performed by the protocol selection unit 304, a notification from the image reception unit 301 indicating completion of reception of an image, a notification indicating completion of image processing performed by the image processing unit 307, or a notification indicating completion of output of an X-ray image performed by the medical information communication circuit 302.

In step S1071, the controller 111 or the X-ray imaging device 106 determines whether the X-ray radiation switch 103 of the X-ray generation apparatus 102 has been pressed. If the X-ray radiation switch 103 has not been pressed, the determination process in steps S106 and S107 is repeated. If the X-ray radiation switch 103 has been pressed, the process proceeds to step S1072, and the X-ray imaging device 106 enters an under-imaging state. Alternatively, the controller 111 causes the imaging apparatus information communication circuit 305 to output a signal for shifting the X-ray imaging device 106 to the under-imaging state and a signal for causing the X-ray controller 104 to generate X-rays. The under-imaging state herein refers to a state in which the pixels included in the sensor array of the X-ray imaging device 106 are in the accumulation state. The under-imaging state may be established by receiving a signal for requesting permission for X-ray radiation, which, as described above, is performed by pressing the X-ray radiation switch 103 of the X-ray generation apparatus 102, or in accordance with detection, by the X-ray imaging device 106, of start of X-ray radiation performed by the X-ray generation apparatus 102. After the X-ray imaging device 106 enters the under-imaging state, the imaging apparatus information communication circuit 305 receives, from the X-ray imaging device 106, information indicating that the "under-imaging state" has been established. At the same time, the X-ray imaging device 106 detects X-rays and accumulates charges obtained as a result of the detection of X-rays. The X-ray imaging device 106 ends the under-imaging state, that is, the accumulation state, after the X-ray radiation ends. The driving circuit and the reading circuit then generate a digital X-ray image.

Thereafter, in step S108, the controller 111 receives the information indicating that the X-ray imaging device 106 has entered the "under-imaging state" and determines that an image is to be received from the X-ray imaging device 106. The controller 111 limits the communication between the medical information communication circuit 302 and the PACS 115.

A timing at which the communication limitation starts need not be a timing at which the X-ray imaging device 106 enters the accumulation state (S105). The timing at which the communication limitation starts may be a timing at which X-ray radiation starts, a timing at which detection of X-rays performed by the sensor ends, or any other timing before the X-ray imaging device 106 begins to transmit an X-ray image. There are various embodiments with respect to the timing at which the communication limitation starts and ends, and such embodiments will be described later with reference to FIGS. 7 to 10.

When the communication between the medical information communication circuit 302 and the PACS 115 is limited, transmission and reception of all pieces of medical information may be stopped. In this case, the communication between the medical information communication circuit 302 and the PACS 115 is disabled. When the communication between the medical information communication circuit 302 and the PACS 115 is disabled, packet communication is unavailable in a communication protocol such as the Transmission Control Protocol/Internet Protocol (TCP/IP) or the User Datagram Protocol (UDP). Such a state is realized by, for example, stopping a function of a wireless antenna. In another embodiment, transmission and reception of part of medical information is stopped. Only transmission of an X-ray image, for example, is stopped. By disabling communication whose communication load can affect the whole communication process, the usability of the system can be maintained. In another embodiment, only transmission of medical information may be stopped, and reception of medical information may be permitted. The transmission of medical information can be stopped when the controller 111 does not output a transmission instruction to the medical information communication circuit 302. Because, unlike image data, the amount of data to be received is usually small and its communication load does not affect the whole communication process, the reception of medical information need not be stopped. In this case, it is possible to allow imaging orders including emergency imaging to be received.

If it is determined in step S1072 that an image begins to be received and the medical information communication circuit 302 is transmitting an X-ray image to be stored in the memory 110, the controller 111 causes the medical information communication circuit 302 to stop transmitting the X-ray image. If N X-ray images are being transmitted and the determination in step S1072 is made while an n-th X-ray image is being transmitted, the transmission of the n-th image is stopped, and the n-th image is transmitted again after the communication limitation is removed. In another embodiment, if image transmission in which reception of image data and sending back of an ACK alternate at certain intervals is performed, data subsequent to data for which an ACK has already been sent back in the n-th image begins to be transmitted after the communication limitation is removed. In these cases, after the transmission of the X-ray image is stopped, the controller 111 causes the image reception unit 301 to begin to receive an image. In doing so, the reception of an image performed by the image reception unit 301 and the transmission of an image performed by the medical information communication circuit 302 are not performed simultaneously, thereby reducing the communication load.

While the communication performed by the medical information communication circuit 302 is limited, the image reception unit 301 begins to receive an image from the X-ray imaging device 106 in step S109. When beginning to receive an image, the image reception unit 301 receives information indicating a data size of the image from the X-ray imaging device 106. At this time, a checksum of the image to be received may be received. After the data is received, an ACK may be sent back. Upon receiving the ACK, the X-ray imaging device 106 begins to transmit the image data, and the image reception unit 301 begins to receive the image.

The timing at which the communication limitation starts may be a timing at which the image reception unit 301 receives a data size or a checksum, a timing at which an ACK is sent back, a timing after a certain period of time has elapsed since the X-ray imaging device 106 transmitted a notification relating to the under-imaging state, or the like. If the accumulation time of the X-ray imaging device 106 is known, for example, the certain period of time may be 50% to 100% of the accumulation time since the reception of an X-ray image does not begin until the accumulation time has elapsed since the notification.

In step S110, the image reception unit 301 completes the reception of the X-ray image from the X-ray imaging device 106. The reception of the X-ray image completes when, for example, data corresponding to the data size received in step S109 is received. Alternatively, the reception of the X-ray image completes when a calculated checksum matches the received checksum. After the reception of the X-ray image completes, the image reception unit 301 transmits an ACK to the X-ray imaging device 106. The reception of the X-ray image thus ends.

In step S111, the limitation of the communication between the medical information communication circuit 302 and the PACS 115 is removed.

Thereafter, the image processing unit 307 performs image processing, and the display controller 306 displays the image subjected to the image processing. The imaging in the imaging protocol selected in step S104 thus ends.

In step S601, it is determined whether the X-ray image received in step S110 is an image to be transmitted to the PACS 115 immediately after the imaging but before an end of the examination, that is, a target of so-called immediate transmission. Whether the X-ray image is a target of immediate transmission is determined on the basis of, for example, a Boolean variable included in the imaging protocol indicating whether the corresponding image is a target of immediate transmission (1) or not (0). If the X-ray image is a target of immediate transmission (YES in S601), the controller 111 causes, in step S602, the medical information communication circuit 302 to begin to transmit the X-ray image to the PACS 115 even before the end of the examination.

In step S112, the controller 111 causes the imaging apparatus information communication circuit 305 to transmit a signal for shifting the X-ray imaging device 106 that has transmitted the X-ray image to the imaging unavailable state.

In step S113, the protocol selection unit 304 cancels the selection of an imaging protocol. After the above-described process, the process returns to step S103.

Imaging operations included in the examination are performed in the above-described manner. X-ray images obtained as a result of the imaging are stored in the memory 110 by the controller 111. After all the imaging operations are completed, the examination ends (YES in S103).

After the end of the examination, the controller 111 determines, in step S603, whether there is an X-ray image that has not been transmitted among the X-ray images stored in the memory 110. The determination is made by determining whether there is an imaging protocol that does not indicate "output" by referring to the state information included in the imaging protocols included in the examination.

If determining that there is an X-ray image that has not been transmitted, the controller 111 causes, in step S604, the medical information communication circuit 302 to transmit, to the PACS 115, the X-ray image that has not been transmitted. After the transmission of the X-ray image is completed, the controller 111 updates the state information included in the imaging protocol corresponding to the transmitted X-ray image to "output". After the transmission of the X-ray image is completed, the imaging control apparatus 107 waits for input of next examination information.

As described above, while the image reception unit 301 is receiving an X-ray image from the X-ray imaging device 106, the communication between the medical information communication circuit 302 and the PACS 115 is limited. X-ray imaging can thus be performed without reducing the throughput of reception of images from the X-ray imaging device 106. If the imaging apparatus information communication circuit 305 and the X-ray imaging device 106 communicate data other than X-ray images, the communication performed by the medical information communication circuit 302 need not be limited.

Figure 7:
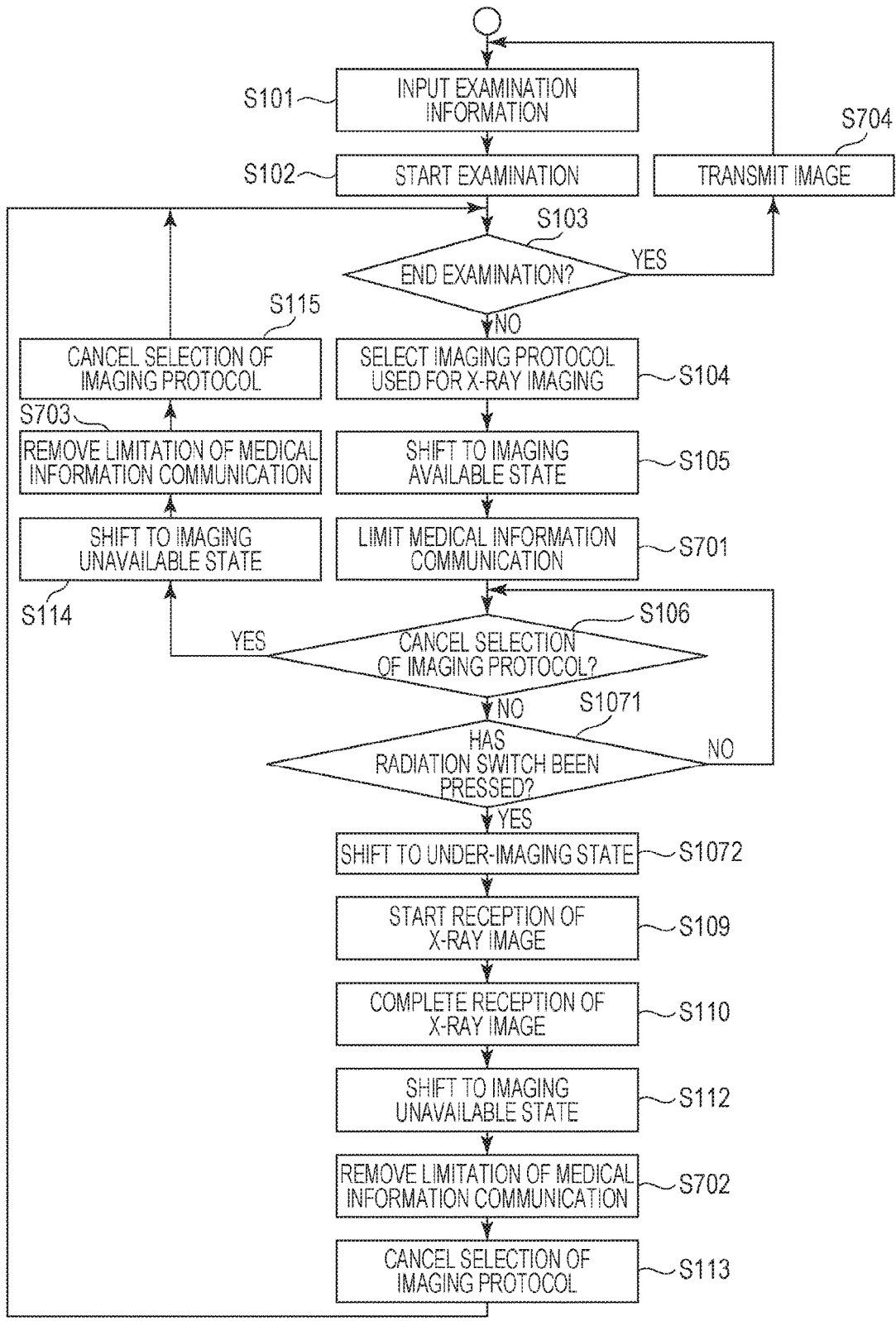
FIG. 7 is a flowchart illustrating a control flow according to another embodiment.
Figure 8:
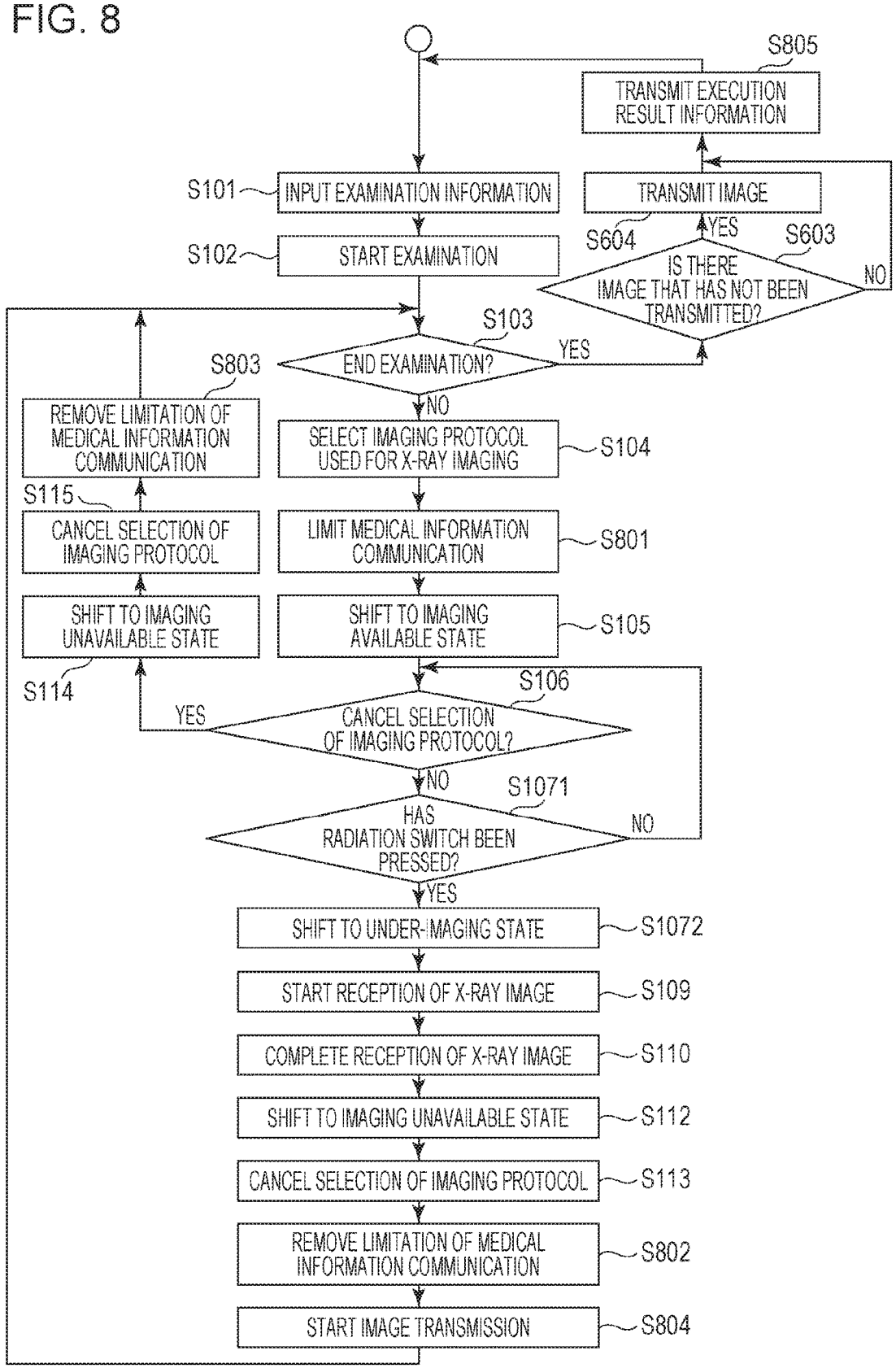
FIG. 8 is a flowchart illustrating a control flow according to another embodiment.
Figure 9:
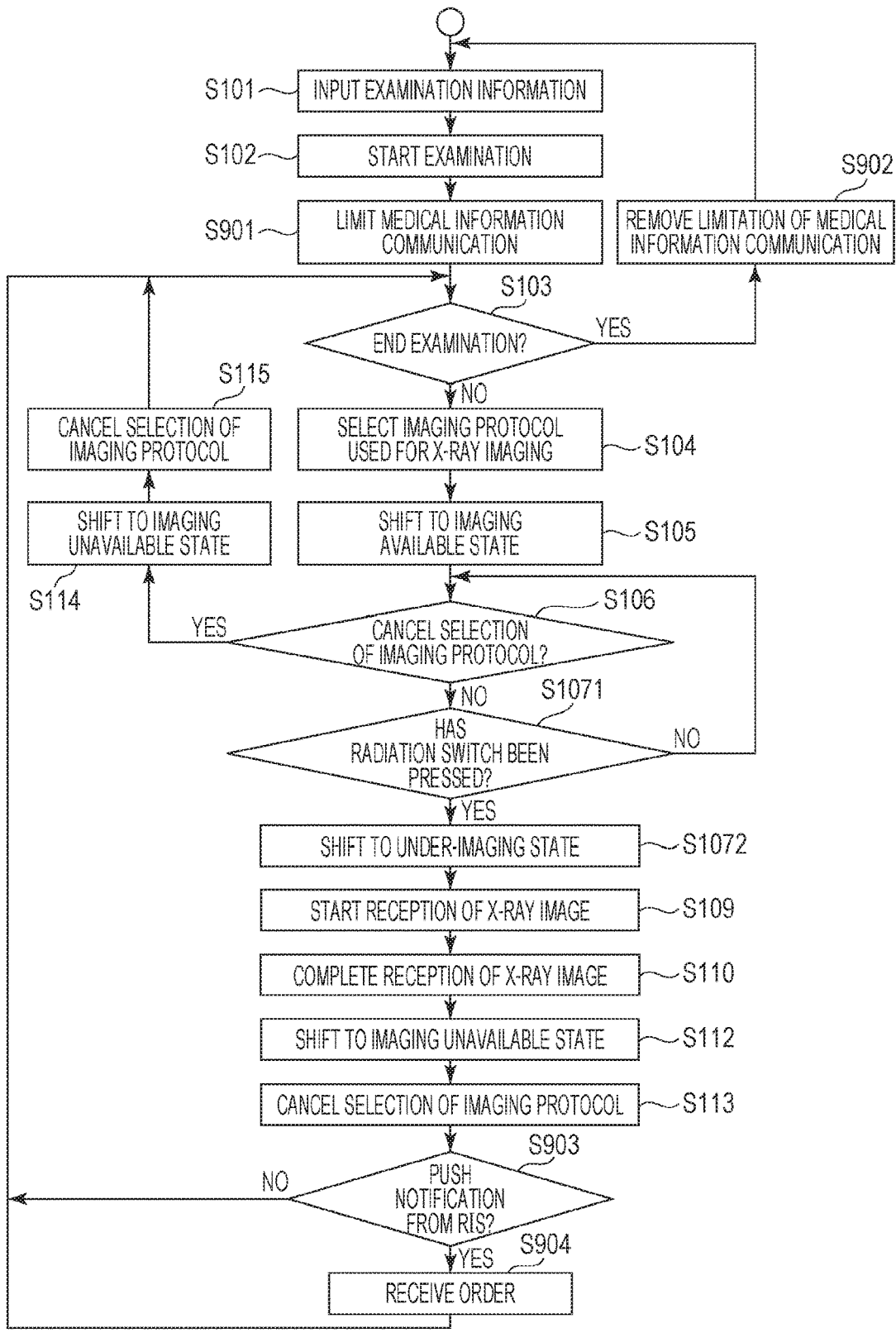
FIG. 9 is a flowchart illustrating a control flow according to another embodiment.

Although the communication with the PACS 115 is limited at a timing immediately before the reception of an X-ray image in the above embodiment, the timing of the communication limitation is not limited to this. FIG. 7 illustrates an embodiment in which the communication is limited after the X-ray imaging device 106 enters the imaging available state. FIG. 8 illustrates an embodiment in which the communication is limited after an imaging protocol is selected. FIG. 9 illustrates an embodiment in which the communication is limited after an examination starts.

A control flow according to another embodiment will be described with reference to the flowchart of FIG. 7. Steps S101 to S106, S1071, S1072, S109, S110, and S112 to S115 are the same as those illustrated in the flowchart of FIG. 6, and description thereof is omitted.

In step S104, an imaging protocol is selected, and the X-ray imaging device 106 enters the imaging available state in step S105. After entering the imaging available state, the X-ray imaging device 106 transmits information indicating that the X-ray imaging device 106 has entered the imaging available state to the imaging control apparatus 107. In step S701, after the imaging apparatus information communication circuit 305 receives the information, the controller 111 limits the communication between the medical information communication circuit 302 and the PACS 115.

Imaging is then performed, and after an X-ray image is received, the X-ray imaging device 106 enters the imaging unavailable state. After entering the imaging unavailable state, the X-ray imaging device 106 transmits information indicating that the X-ray imaging device 106 has entered the imaging unavailable state to the imaging control apparatus 107. In step S702, after the imaging apparatus information communication circuit 305 receives the information, the controller 111 removes the limitation of the communication between the medical information communication circuit 302 and the PACS 115.

The same holds when an instruction to cancel the selection of an imaging protocol is issued in step S106 (YES in S106) and the X-ray imaging device 106 enters the imaging unavailable state in step S114. That is, in step S703, after the imaging apparatus information communication circuit 305 receives a signal indicating that the X-ray imaging device 106 has entered the imaging unavailable state, the controller 111 removes the limitation of the communication between the medical information communication circuit 302 and the PACS 115.

After all the imaging operations are completed and the examination ends (YES in step S103), the medical information communication circuit 302 transmits, in step S704, X-ray images obtained as a result of the examination to the PACS 115 in accordance with control performed by the controller 111.

Figure 6:
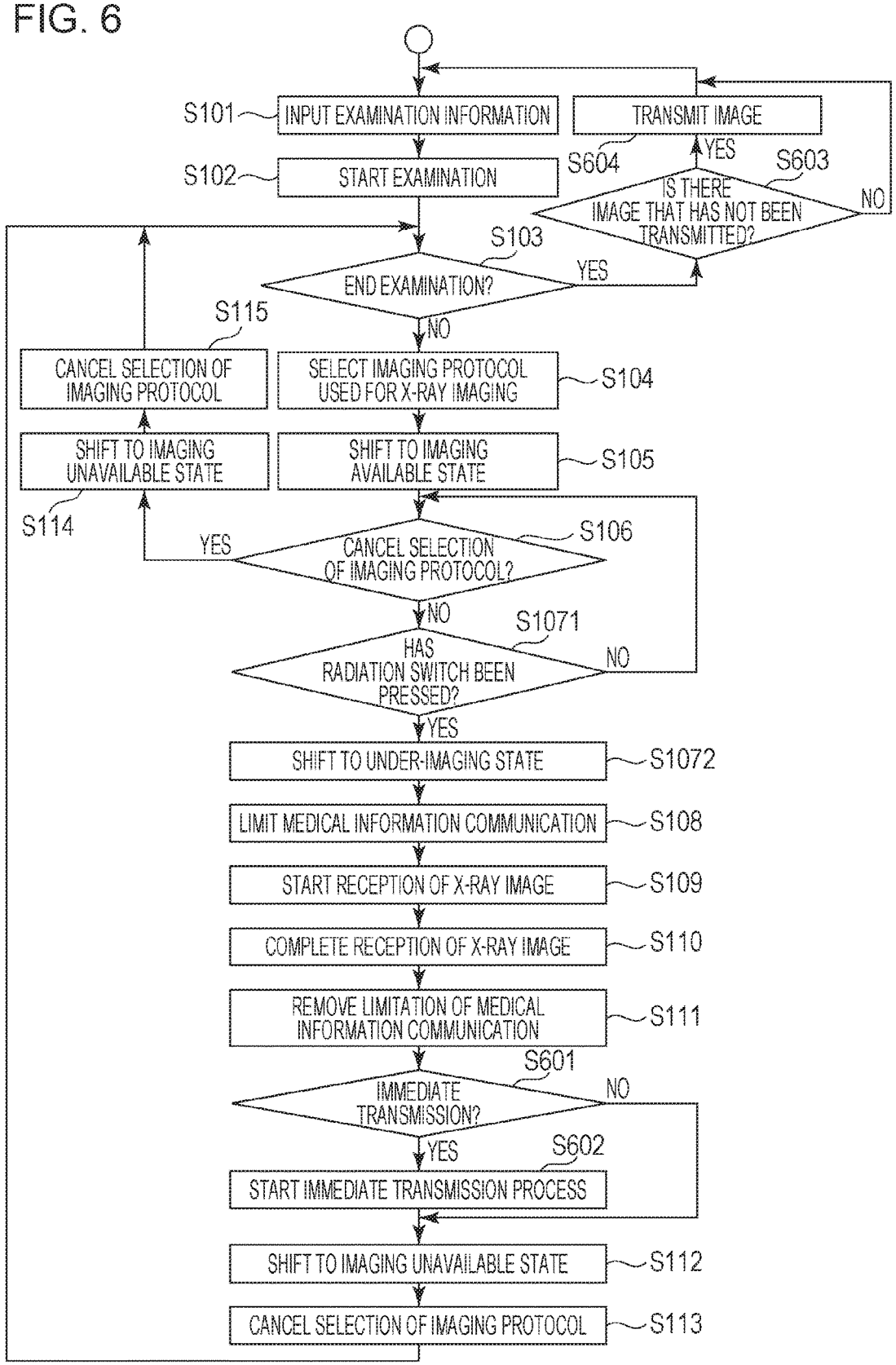
FIG. 6 is a flowchart illustrating a control flow according to an embodiment.

Since the X-ray imaging device 106 enters the imaging unavailable state (S112) after each imaging operation ends, the immediate transmission in steps S601 and S602 illustrated in FIG. 6 may be performed thereafter. Alternatively, if a next imaging operation is performed without performing the immediate transmission in order to give priority to the throughput of the imaging, the function of the immediate transmission may be disabled. Information regarding the function of the immediate transmission is stored in the memory 110 as setting information that can be enabled or disabled in accordance with an operation input by the operator. If the function of the immediate transmission is off, a result of the determination in step S601 is invariably NO, and the immediate transmission is not performed.

As described above, in the present embodiment, if imaging conditions (imaging protocol) used for the imaging are selected in step S104, the controller 111 limits the transmission of an image stored in the memory 110 to the PACS 115 in step S108 after the X-ray imaging device 106 completes preparation for the imaging (enters the imaging available state) in step S105. In another embodiment, the X-ray imaging device 106 may always be in the imaging available state, and the transmission of an image to the PACS 115 may be limited in accordance with the selection of an imaging protocol. Alternatively, a button for inputting an operation for shifting the X-ray imaging device 106 to the imaging available state may be provided separately from the selection of an imaging protocol, and the controller 111 may limit the transmission of an image to the PACS 115 if the button is pressed.

As described above, if the X-ray imaging device 106 is in the imaging available state or the under-imaging state, the communication between the medical information communication circuit 302 and an external medical information management server is limited, and X-ray imaging can be performed without reducing the throughput of reception of an image.

A control flow according to another embodiment will be described with reference to the flowchart of FIG. 8. Steps S101 to S106, S1071, S1072, S109, S110, and S112 to S115 are the same as those illustrated in the flowchart of FIG. 6, and description thereof is omitted.

After an imaging protocol used for X-ray imaging is selected, the communication between the medical information communication circuit 302 and the PACS 115 is limited in step S801. In step S105, the controller 111 causes the imaging apparatus information communication circuit 305 to output a signal to the X-ray imaging device 106 on the basis of the selected imaging protocol to shift the X-ray imaging device 106 to the imaging available state.

After the imaging for the imaging protocol selected in step S104 ends, the protocol selection unit 304 cancels the selection of an imaging protocol in step S113. In step S802, the controller 111 removes the limitation of the communication between the medical information communication circuit 302 and the PACS 115. After the above-described process, the process returns to step S103.

The same holds when an instruction to cancel the selection of an imaging protocol is issued in step S106 (YES in S106) and the protocol selection unit 304 cancels the selection of an imaging protocol in step S115. That is, after the selection of an imaging protocol is canceled, the controller 111 removes, in step S803, the limitation of the communication between the medical information communication circuit 302 and the PACS 115.

In step S804, the medical information communication circuit 302 transmits the X-ray images obtained as a result of the imaging to the PACS 115.

After the end of the examination (YES in step S103), the X-ray images are transmitted (S603 and S604) as in the embodiment illustrated in FIG. 6. After the X-ray images are transmitted, the medical information communication circuit 302 transmits execution result information to the HIS/RIS 114 in step S805. That is, the medical information communication circuit 302 transmits information including a notification indicating that the examination has ended and information including a radiation dose used for the subject in the examination to the HIS/RIS 114 as execution result information in accordance with control performed by the controller 111.

As described above, when an imaging protocol to be used is selected, the communication between the medical information communication circuit 302 and an external medical information management server is limited, and X-ray imaging can be performed without reducing the throughput of the reception of an image.

As described above, in the present embodiment, after the X-ray imaging device 106 enters the imaging unavailable state in step S112 and the selection of imaging conditions (imaging protocol) used for imaging is canceled in step S113, the controller 111 removes the limitation of the transmission of an image stored in the memory 110 to the PACS 115 in step S802. In another embodiment, the X-ray imaging device 106 may always be in the imaging available state, and the transmission of an image to the PACS 115 may be limited after the selection of an imaging protocol is canceled. Alternatively, a button for inputting an operation for shifting the X-ray imaging device 106 to the imaging unavailable state may be provided separately from the cancelation of the selection of an imaging protocol, and the controller 111 may remove the limitation of the transmission of an image to the PACS 115 if the button is pressed.

A control flow according to another embodiment will be described with reference to the flowchart of FIG. 9.

Steps S101 to S106, S1071, S1072, S109, S110, and S112 to S115 are the same as those illustrated in the flowchart of FIG. 6, and description thereof is omitted.

After the examination starts in step S102, the controller 111 limits the communication between the medical information communication circuit 302 and the PACS 115 in step S901. Since transmission of an image to the PACS 115 is basically inhibited during the examination, the function of the immediate transmission is disabled.

After the examination ends (YES in S103), the controller 111 removes the limitation of the communication between the medical information communication circuit 302 and the PACS 115 in step S902.

Transmission of an examination start notification to the HIS/RIS 114 is not limited. In one embodiment, the controller 111 causes the medical information communication circuit 302 to transmit, to the HIS/RIS 114, information (examination start notification) indicating that the examination has started.

In another embodiment, after the selection of an imaging protocol is canceled (S113) at an end of an imaging operation, the controller 111 determines whether there has been a push transmission notification regarding examination information (imaging order) from the HIS/RIS 114 (S903). This determination is made on the basis of whether the medical information communication circuit 302 has received a push transmission notification from the HIS/RIS 114.

If there has been a push transmission notification (YES in S903), the controller 111 receives, in step S904, the examination information (imaging order) with the medical information communication circuit 302. If there has not been a push transmission notification, the process proceeds to step S103.

As described above, during the examination, the communication between the medical information communication circuit 302 and an external medical information management server is limited, and X-ray imaging can be performed without reducing the throughput of the reception of an image.

Methods for determining start and end of the communication limitation are not limited to those described above. The user may, for example, select timings at which the communication limitation starts and ends from a plurality of candidates and determine the selected information as setting information. A timing at which the communication limitation starts may be, for example, (1-1) selection of imaging conditions (imaging protocol) used for imaging, (1-2) completion of preparation for imaging in the X-ray imaging device 106, (1-3) a shift of the X-ray imaging device 106 to the accumulation state, (1-4) generation of X-rays performed by the X-ray generation apparatus 102, (1-5) completion of detection of X-rays performed by the X-ray imaging device 106, or the like. A timing at which the communication limitation ends may be, for example, (2-1) completion of reception of an image, (2-2) cancelation of selection of imaging conditions (imaging protocol) used for imaging, (2-3) a shift of the X-ray imaging device 106 to the imaging unavailable state, or the like. The controller 111 selects information from these candidates for setting information regarding timings in accordance with an operation input by the operator, for example, and determines the selected information as setting information. The controller 111 then determines whether an event corresponding to the setting information has occurred. If an event corresponding to the setting information has occurred, the controller 111 begins to limit the communication and then removes the limitation. Alternatively, either the timing at which the communication limitation starts or the timing at which the communication limitation ends may be a timing at which a certain event occurs, and the other timing may be determined on the basis of the setting information.

Although the transmission of an image to the PACS 115 is inhibited during the communication limitation in the above embodiments, embodiments of the present invention are not limited to this. Even if the communication is limited during an examination and the function of the immediate transmission is disabled (the embodiment illustrated in FIG. 9), for example, the controller 111 may permit the immediate transmission for images of high priority, thereby realizing prompt diagnoses. The controller 111 controls whether to transmit an image obtained by the X-ray imaging device 106 to the image storage apparatus in accordance with whether the image is associated with first identification information. In one embodiment, the first identification information is priority flag information, which indicates that an image associated therewith is an image given priority in transmission, and the priority flag information may be included in an imaging protocol. The controller 111 does not prevent the medical information communication circuit 302 from transmitting X-ray images associated with imaging protocols including the priority flag information to the PACS 115 even during the communication limitation. The controller 111 limits only transmission of X-ray images corresponding to imaging protocols that do not include the priority flag information to the PACS 115 during the communication limitation. In another embodiment, the first identification information is non-priority flag information, which indicates that an image associated therewith is not to be transmitted to the PACS 115 during the communication limitation. The controller 111 prevents the medical information communication circuit 302 from transmitting X-ray images associated with imaging protocols including the non-priority flag information to the PACS 115 during the communication limitation. The controller 111 does not prevent the medical information communication circuit 302 from transmitting X-ray images associated with imaging protocols that do not include the non-priority flag information to the PACS 115 even during the communication limitation. Alternatively, the first identification information may be flag information having a Boolean variable indicating whether an image associated therewith is an image given priority in transmission (1) or not (0). If the image is given priority (if the Boolean variable is 1), the image may be transmitted even during the communication limitation.

While the X-ray imaging device 106 is transmitting an X-ray image to the imaging control apparatus 107, the transmission of the X-ray image may be given priority even if the priority flag information is associated with another X-ray image. The X-ray image associated with the priority flag information may be transmitted to the PACS 115 in other periods during the communication limitation. The controller 111 controls the transmission.

In another embodiment, when a plurality of X-ray images are sequentially transmitted to the PACS 115 after an end of an examination, the X-ray images may be transmitted to the PACS 115 in order of priority. If a plurality of images obtained by the X-ray imaging device 106 are stored in the memory 110, for example, the controller 111 controls the order of transmission of the plurality of images on the basis of whether each of the plurality of images is associated with second identification information. The second identification information may be the priority flag information, which indicates that an image associated therewith is an image given priority in transmission, the non-priority flag information, which indicates that the image associated therewith is not given priority in transmission, or the flag information having a Boolean variable indicating whether the image associated therewith is an image given priority in transmission (1) or not (0). The controller 111, for example, refers to the second identification information included in each of a plurality of image protocols and determines whether a corresponding X-ray image is an image given priority in transmission. The controller 111 then determines the order of transmission of the images in accordance with results of the determinations and transmits the images in order of priority.

In another embodiment, if additional transmission of medical information relating to the limitation is requested when the communication between the medical information communication circuit 302 and the PACS 115 is limited, imaging may be temporarily stopped, and the transmission of the medical information may be performed first. While an image stored in the memory 110 is being transmitted to the PACS 115, for example, the controller 111 limits reception of an image from the X-ray imaging device 106.

Figure 10:
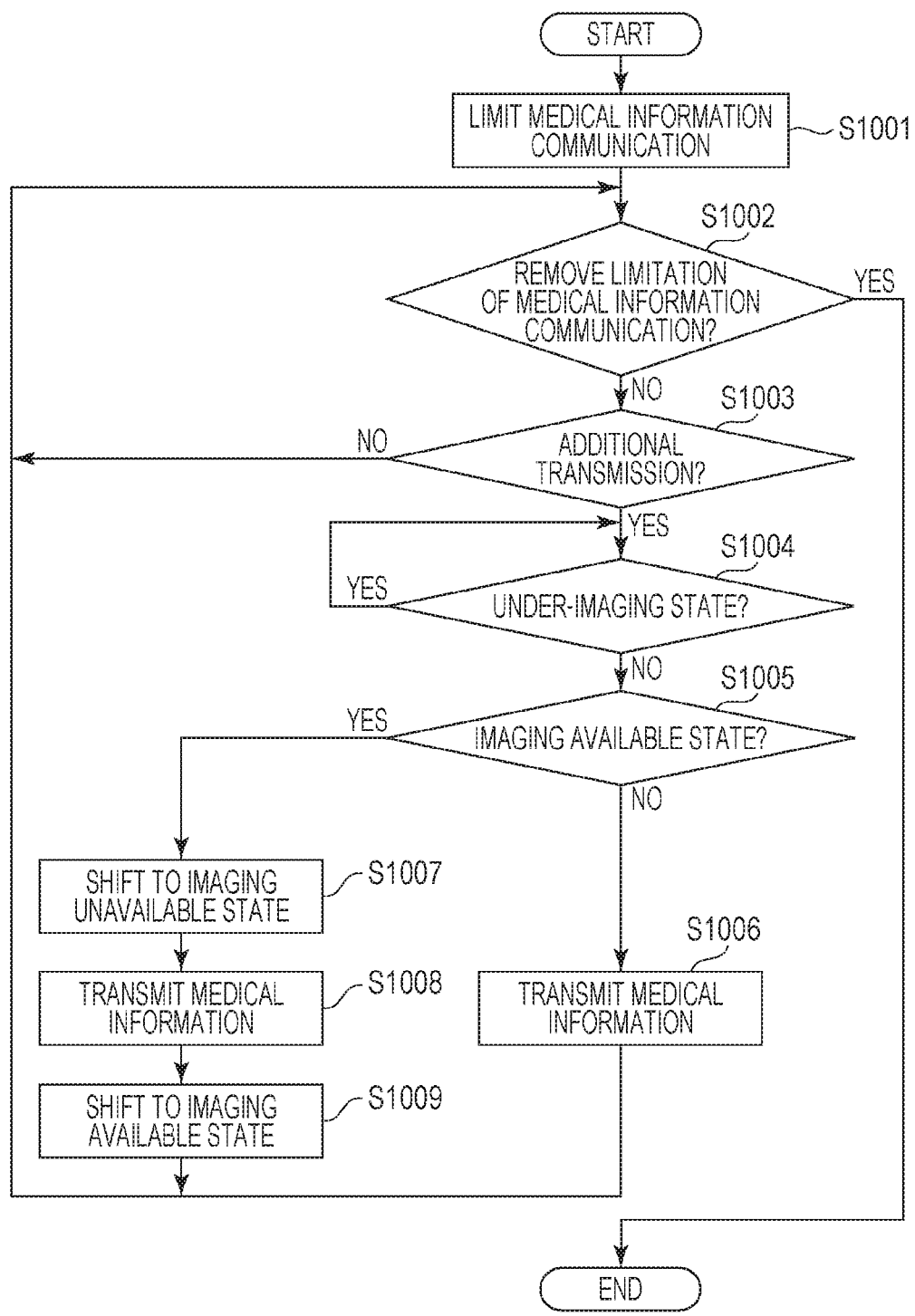
FIG. 10 is a flowchart illustrating a control flow according to another embodiment.

A control flow according to another embodiment will be described with reference to the flowchart of FIG. 10.

First, in step S1001, the controller 111 limits the communication between the medical information communication circuit 302 and the PACS 115.

In step S1002, the controller 111 determines whether the limitation of the communication performed by the medical information communication circuit 302 has been removed. If the communication limitation has been removed, the process ends. If not, the process proceeds to step S1003.

In step S1003, the controller 111 determines whether there has been a request for additional transmission to the medical information communication circuit 302. If the communication limitation has not been removed and there has been a request for additional transmission, the process proceeds to step S1004.

In step S1004 and later, the state of the X-ray imaging device 106 is determined in order to perform a transmission process in response to the request for additional transmission. In step S1004, if the X-ray imaging device 106 is in the under-imaging state, the controller 111 waits until the X-ray imaging device 106 gets out of the under-imaging state. If the controller 111 determines that the X-ray imaging device 106 has gotten out of the under-imaging state, the process proceeds to step S1005.

In step S1005, the controller 111 determines whether the X-ray imaging device 106 is in the imaging available state. If the controller 111 determines that the X-ray imaging device 106 is not in the imaging available state (NO in step S1005), the medical information communication circuit 302 transmits medical information such as an X-ray image to the PACS 115, and the process returns to step S1002. If the controller 111 determines that the X-ray imaging device 106 is in the imaging available state (YES in step S1005), the controller 111 causes the imaging apparatus information communication circuit 305 to transmit a signal to shift the X-ray imaging device 106 to the imaging unavailable state.

In step S1008, the medical information communication circuit 302 transmits medical information such as an X-ray image to the PACS 115. After the transmission ends, the controller 111 shifts, in step S1009, the X-ray imaging device 106 to the imaging available state in accordance with an instruction from the imaging apparatus information communication circuit 305, and the process returns to step S1002.

As described above, by transmitting medical information before X-ray imaging, control can be performed without reducing throughput in the X-ray imaging.

Figure 11:
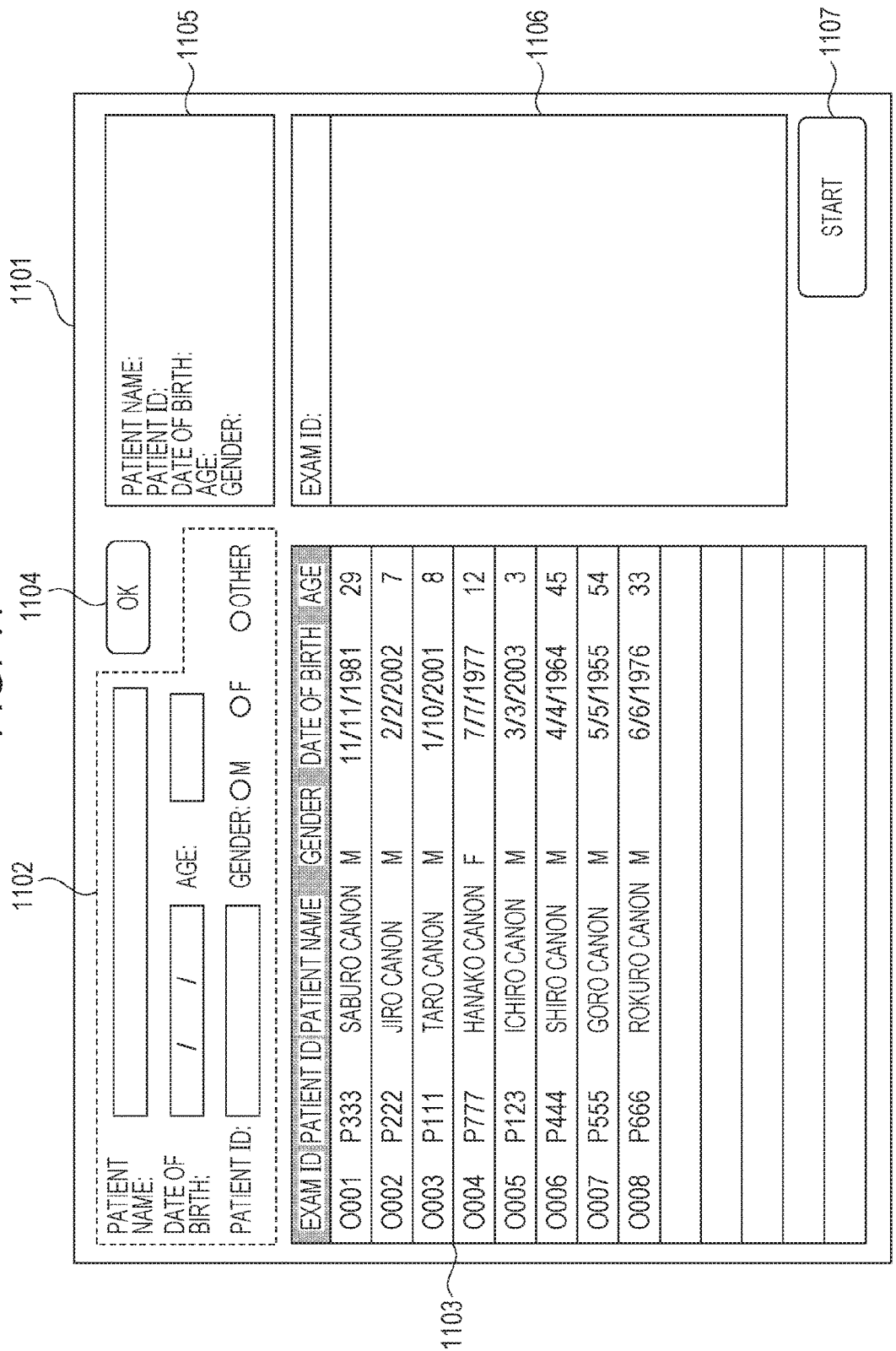
FIG. 11 is a diagram illustrating an example of an examination information input screen according to an embodiment.

FIG. 11 illustrates an example of an examination information input screen 1101, which is a GUI used for inputting examination information and starting an examination. The examination information input screen 1101 is a screen for inputting information regarding a patient to be subjected to an examination. The examination information input screen 1101 includes a patient information input area 1102, a patient information list 1103, a patient information confirmation button 1104, a patient information display area 1105, an examination information display area 1106, and an examination start button 1107. The patient information input area 1102 is an area in which values of items included in the patient information are input or selected. The patient information list 1103 is a list of patient information used for examinations conducted in the past. Each column of the patient information list 1103 corresponds to one of the items included in the patient information. Each row of the patient information list 1103 indicates patient information regarding a patient. If one of the pieces of patient information in the patient information list 1103 is selected, the selected piece of patient information is input to the items in the patient information input area 1102. The patient information confirmation button 1104 is a button or an icon for confirming the values input to the patient information input area 1102 as patient information. If the patient information confirmation button 1104 is pressed, it is determined whether values are input to required items or whether the input values are acceptable. If there is no problem, the values are confirmed as patient information. The patient information display area 1105 is an area in which confirmed patient information is displayed. No values are displayed in items until values are confirmed as patient information, and, after patient information is determined, values are displayed. The examination information display area 1106 is an area in which input examination information is displayed. The examination information includes information for identifying an examination, such as an examination ID, an inquiring doctor's name, an interpreting doctor's name, description of the examination, and an institution name. The examination information also includes an imaging technique selected in advance. The examination information display area 1106 includes a part in which items of the examination information are displayed and a part in which information regarding an imaging protocol corresponding to an imaging protocol ID included in the examination information is displayed. No information is displayed in the examination information display area 1106 until examination information is input. A plurality of examinations may start at once. In this case, examination information display areas 1106 as many as the number of examinations are displayed side by side.

The examination start button 1107 is a button or an icon for inputting an operation for starting an examination including at least one imaging operation for a subject. If the examination start button 1107 is pressed, the controller 111 determines whether patient information and examination information have been input. If there is no problem, the examination starts. The display controller 306 displays, on the display unit 109, an imaging screen 1201 for performing imaging on the subject.

If a (first) operation, in which the examination start button 1107 is pressed, is input or the imaging screen 1201 is displayed in the embodiment illustrated in FIG. 9, for example, the controller 111 limits the transmission of an image to the PACS 115.

Figure 12:
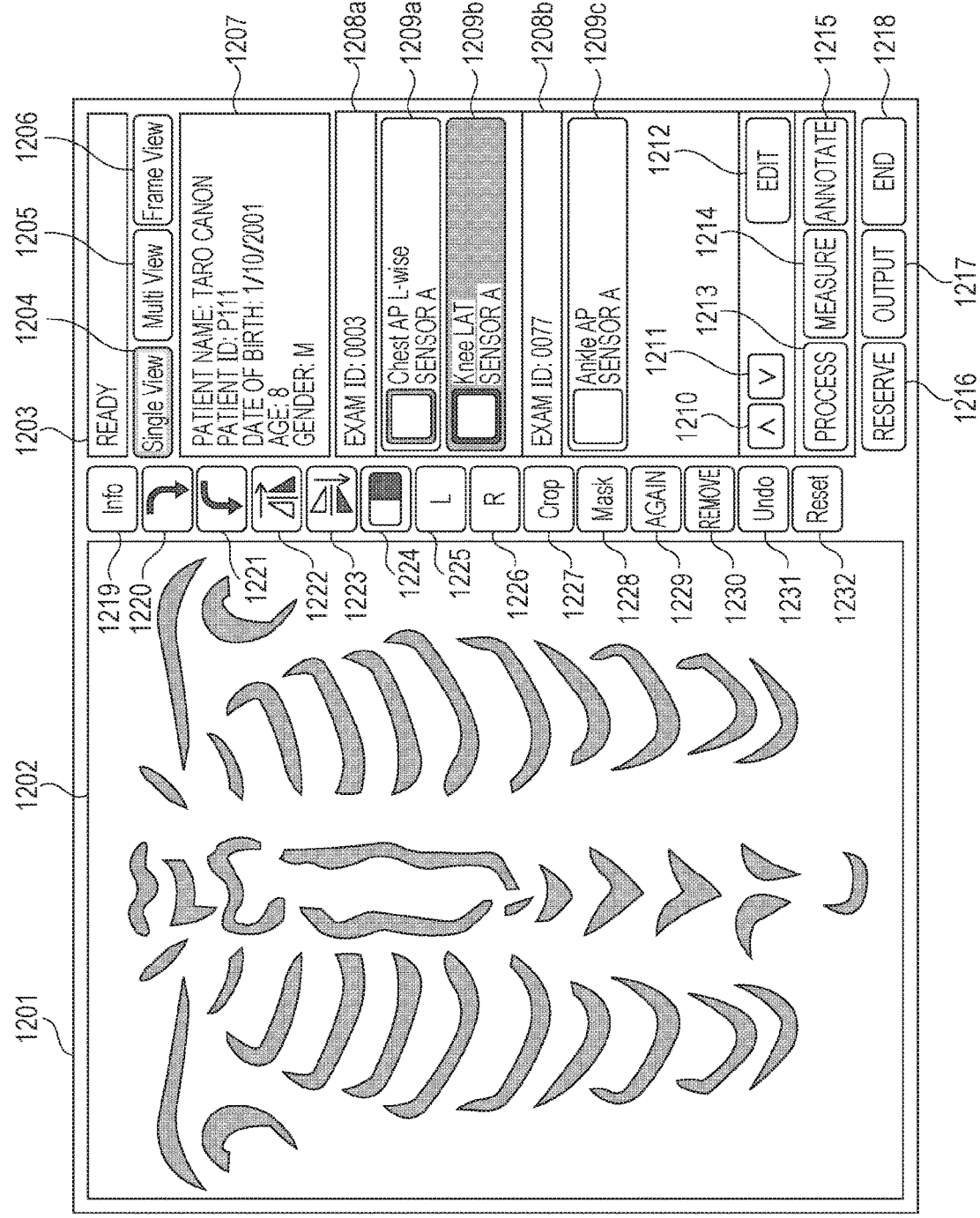
FIG. 12 is a diagram illustrating an example of an imaging screen according to an embodiment.

FIG. 12 illustrates an example of the imaging screen 1201, which is displayed by the display controller 306, for performing at least one imaging operation on a subject. The imaging screen 1201 includes an image display area 1202, a status display area 1203, a single-view button 1204, a multi-view button 1205, a frame view button 1206, a patient information display area 1207, examination information display areas 1208a and 1208b, imaging technique display areas 1209a and 1209b, an imaging technique use order up button 1210, an imaging technique use order down button 1211, an examination edit button 1212, an image processing button 1213, a measurement button 1214, an annotation edit button 1215, an examination reserve button 1216, an image output button 1217, an examination end button 1218, an annotation display switching button 1219, a right turn button 1220, a left turn button 1221, a horizontal reversal button 1222, a vertical reversal button 1223, a black-white reversal button 1224, an L mark input button 1225, an R mark input button 1226, a crop button 1227, a mask process button 1228, a re-imaging button 1229, a remove button 1230, an undo button 1231, and a reset button 1232. In the image display area 1202, a captured X-ray image is displayed as a preview. If preview selection is switched after imaging, an X-ray image selected as a result of the switching is displayed as a preview. Patient information, examination information, radiation conditions, and the like are displayed as annotations in accordance with settings. In an initial state immediately after a start of an examination, an image is not displayed. The status display area 1203 is an area in which statuses transmitted from the X-ray controller 104 and the X-ray imaging device 106 are displayed using unique colors and letters so that the operator can easily understand current status. The display controller 306 that has received status notifications from the X-ray controller 104 and the X-ray imaging device 106 through the display unit 212 notifies the image processing unit 307 of changes in statuses. The image processing unit 307 determines display content on the basis of a combination of the statuses transmitted from the X-ray controller 104 and the X-ray imaging device 106 and transmits an instruction to change status display to an input/output controller. If the X-ray controller 104 cannot radiate X-rays and the X-ray imaging device 106 is in the imaging unavailable state, for example, "Not Ready" is displayed as sensor status. If the X-ray controller 104 can radiate X-rays and the X-ray imaging device 106 is in the imaging available state, "Ready" is displayed as the sensor status, and a background color is changed so that the operator can easily distinguish "Ready" from "Not Ready". The single-view button 1204 is a button or an icon for switching to single view, in which a frame of an image displayed in the image display area 1202 as a preview. In the case of an image including a plurality of frames, another frame can be displayed or a moving image can be played back using a keyboard or a mouse when a preview is displayed. The multi-view button 1205 is a button or an icon for switching to multi-view, in which the image display area 1202 is divided into a plurality of display areas arranged in a matrix and images obtained as a result of an examination that is being conducted are displayed at the same time. The multi-view button 1205 is invalid and the multi-view is unavailable unless two or more images are obtained in an examination that is being conducted. The frame view button 1206 is a button or an icon for switching to frame view, in which the image display area 1202 is divided into a plurality of display areas arranged in a matrix and frame images of a moving image selected as a preview are displayed at the same time. If an image selected as a preview is not a moving image, the frame view button 1206 is invalid and the frame view is unavailable. The patient information display area 1207 is an area in which patient information such as a patient name and a patient ID is displayed. In the examination information display areas 1208a and 1208b, examination information such as an examination ID and description of the examination is displayed. In the imaging technique display areas 1209a and 1209b, imaging techniques selected in an examination are displayed. In the imaging technique display area 1209, imaging technique information such as an imaging technique name and all image thumbnails obtained as a result of imaging are displayed. The imaging technique display areas 1209a and 1209b also include, before imaging starts, imaging target thumbnails and, after imaging ends, image thumbnails. The imaging technique use order up button 1210 is a button or an icon for advancing an imaging technique in order of use. If the imaging technique use order up button 1210 is pressed with an imaging technique display area 1209b selected, the selected imaging technique display area 1209b goes above another imaging technique display area 1209a displayed above. If the first imaging technique display area 1209a in an examination is selected, however, the imaging technique display area 1209a does not go up. The imaging technique use order down button 1211 is a button or an icon for delaying an imaging technique in order of use. If the imaging technique use order down button 1211 is pressed with the imaging technique display area 1209a selected, the selected imaging technique display area 1209a goes below the imaging technique display area 1209b displayed below. If the last imaging technique display area 1209b in an examination is selected, however, the imaging technique display area 1209b does not go down. The examination edit button 1212 is a button or an icon for shifting to an imaging technique selection screen in order to edit an examination. The image processing button 1213 is a button or an icon for displaying or closing an image processing operation unit. The measurement button 1214 is a button or an icon for displaying or closing a measurement operation unit. The annotation edit button 1215 is a button or an icon for displaying or closing an annotation operation unit. The examination reserve button 1216 is a button or an icon for reserving an examination that is being conducted. The image output button 1217 is a button or an icon for outputting an image obtained as a result of an examination that is being performed. The examination end button 1218 is a button or an icon for receiving a (second) operation for ending an examination including at least one imaging operation. The annotation display switching button 1219 is a button or an icon for displaying or closing annotations in the image display area 1202. The right turn button 1220 is a button or an icon for turning right an image displayed as a preview. The left turn button 1221 is a button or an icon for turning left an image displayed as a preview. The horizontal reversal button 1222 is a button or an icon for horizontally reversing an image displayed as a preview. The vertical reversal button 1223 is a button or an icon for vertically reversing an image displayed as a preview. The black-white reversal button 1224 is a button or an icon for reversing window values of an image displayed as a preview. The L mark input button 1225 is a button or an icon for inputting a lateral marker "L" to an image displayed as a preview. The L mark input button 1225 can be turned on and off, that is, "L" is input when the L mark input button 1225 is turned on, and "L" is removed when the L mark input button 1225 is turned off. The R mark input button 1226 is a button or an icon for inputting a lateral marker "R" to an image displayed as a preview. The R mark input button 1226 can be turned on and off, that is, "R" is input when the R mark input button 1226 is turned on, and "R" is removed when the R mark input button 1226 is turned off. The crop button 1227 is a button or an icon for cropping a region of interest from an image displayed as a preview. The mask process button 1228 is a button or an icon for performing a mask process on an image displayed as a preview. The re-imaging button 1229 is a button or an icon for performing re-imaging on an imaging technique including an image displayed as a preview. The re-imaging refers to a process for removing an image to be re-imaged and a process for newly adding the same imaging technique. The remove button 1230 is a button or an icon for removing an image displayed as a preview. If the removal process is performed, a removal setting included in image information is turned on. The undo button 1231 is a button or an icon for performing an undo process, which rearranges a processing history of an image displayed as a preview chronologically. The reset button 1232 is a button or an icon for removing all steps of processing performed on an image displayed as a preview and performing a reset process, which restores a state immediately after imaging. The imaging screen 1201 configured as described above is displayed.

In the embodiment illustrated in FIG. 9, for example, the controller 111 removes the limitation of the transmission of an image to the PACS 115 in accordance with at least either an operation input using the examination end button 1218 or an end of display of the imaging screen 1201.

Figure 13:
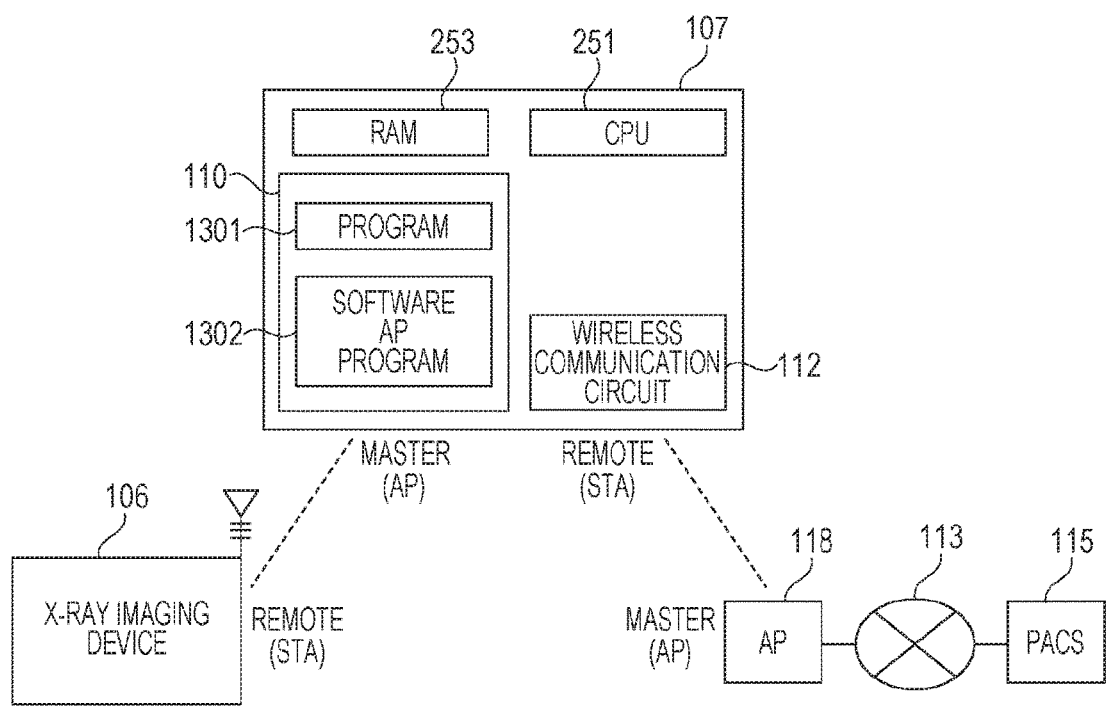
FIG. 13 is a diagram illustrating the configuration of an X-ray imaging system according to another embodiment.

FIG. 13 illustrates another example of a hardware configuration according to an embodiment of the present embodiment. Description of components given the same reference numerals as those illustrated in FIG. 1 or 2 is omitted. A hospital system according to the present embodiment includes the X-ray imaging device 106, the imaging control apparatus 107, the hospital AP 118 that connects the network 113 and the imaging control apparatus 107 with each other, and the PACS 115.

The imaging control apparatus 107 includes the CPU 251, the RAM 253, the memory 110, and the wireless communication circuit 112. In the memory 110, a program 1301 for realizing the operation according to the above embodiments and a software AP program 1302 for operating the wireless communication circuit 112 as an access point are stored. The programs 1301 and 1302 are loaded into the RAM 253 and executed by the CPU 251.

The wireless communication circuit 112 includes a single wireless communication module, which is used for communicating with both the X-ray imaging device 106 and the PACS 115 through a single communication channel. In this case, since the hospital AP 118 operates as a master station (access point), the wireless communication circuit 112 that communicates with the hospital AP 118 operates as a remote station. Since the wireless communication circuit of the X-ray imaging device 106 operates as a remove station, the wireless communication circuit 112 operates as a master station (access point) using the software AP program 1302. In doing so, the imaging control apparatus 107 can communicate with both the X-ray imaging device 106 and the network 113 using the single wireless communication module.

Other embodiments will be described hereinafter.

Although an imaging apparatus that performs X-ray imaging has been described in the above embodiments, aspects of the present invention are not limited to this. Embodiments also include medical imaging apparatuses other than the X-ray imaging apparatus, for example, such as an ultrasonic imaging apparatus including an ultrasonic probe that operates without a cable. In this case, a control apparatus that wirelessly communicates with the ultrasonic probe, which is an imaging device, of the ultrasonic imaging apparatus corresponds to the imaging control apparatus 107 according to the above embodiments of the present embodiment.

Although the imaging control apparatus 107 transmits a medical image to the PACS 115 in most of the above embodiment, the destination of a medical image is not limited to this. A medical image may be transmitted to an image storage apparatus that wirelessly communicates with the imaging control apparatus 107, such as a work station.

In the above embodiments, the X-ray imaging device 106 and the imaging control apparatus 107 may perform remote-master (station-AP) communication, or may perform ad hoc communication.

In an X-ray imaging system according to one embodiment, the X-ray imaging device 106 is directly connected to the hospital AP 118 without using the imaging control apparatus 107 and transmits an image to the PACS 115. In this case, the X-ray imaging device 106 transmits a reduced image of an image obtained as a result of imaging to the imaging control apparatus 107. At this time, a control section of the X-ray imaging device 106 limits the transmission of an X-ray image to the PACS 115 while the X-ray imaging device 106 is transmitting the reduced image to the imaging control apparatus 107, thereby reducing a communication delay due to a communication overlap. A prompt checking of an image obtained as a result of imaging can thus be realized, and the efficiency of imaging can be improved.

Although only one imaging control apparatus 107 is used in the above embodiments, a control system including a plurality of information processing apparatuses realizes the functions of the imaging control apparatus 107 in another embodiment. In this case, the plurality of information processing apparatuses each include a communication circuit and can communicate with one another using the communication circuits. One of the plurality of information processing apparatuses may function as the image processing unit 307, and another may function as the controller 111. The plurality of information processing apparatuses need to be able to communicate at a certain communication rate, but need not be located in the same hospital or the same country. In such a control system, for example, the image processing unit 307 may be a server apparatus or servers shared by the plurality of information processing apparatuses.

Aspects of the present invention also include an embodiment in which a software program for realizing the functions according to the above embodiments is directly or remotely supplied to a system or an apparatus and a computer of the system or the apparatus reads and executes program codes included in the supplied software program.

That is, the program codes installed on the computer in order to realize the functions and processes in aspects of the present invention are also an embodiment of the present invention. In addition, the functions according to the above embodiments can be realized by performing, using an operating system (OS) or the like operating on the computer, part or all of the actual processes on the basis instructions included in the program read by the computer.

Embodiments obtained by appropriately combining the above embodiments are also embodiments of the present invention.

While aspects of the present invention have been described with reference to exemplary embodiments, it is to be understood that aspects of the invention are not limited to the disclosed exemplary embodiments. The scope of the following claims is to be accorded the broadest interpretation so as to encompass all such modifications and equivalent structures and functions.

This application claims the benefit of Japanese Patent Application No. 2014-253502 filed Dec. 15, 2014, which is hereby incorporated by reference herein in its entirety.

What is claimed is:

1. A control apparatus that controls an imaging device that obtains an image using a sensor with a plurality of pixels arranged in two dimensions, the control apparatus comprising:
    a wireless communication circuit configured to communicate with the imaging device and an external image storage apparatus;
    a memory configured to store an image based on an image transmitted from the imaging device and received by the wireless communication circuit;
    an examination information input unit configured to obtain examination information including information about an examination state by receiving information from an external apparatus, the information about the examination state being information for managing a state of an examination including at least one imaging operation for the subject, and the external apparatus being different from the imaging device; and
    a controller configured to limit transmission of the image stored in the memory to the external image storage apparatus if the information about the examination state is changed for starting the examination.

2. The control apparatus according to claim 1,
    wherein the controller performs control such that the wireless communication circuit does not transmit the image stored in the memory, and
    wherein, if a communication cable is connected to the control apparatus, the controller causes the wireless communication circuit to transmit the image stored in the memory through the communication cable even while the wireless communication circuit is receiving an image.

3. The control apparatus according to claim 1,
    wherein, while the wireless communication circuit is receiving an image from the imaging device, the controller limits the transmission of the image stored in the memory to the external image storage apparatus and causes the wireless communication circuit to at least either receive an imaging order from an external apparatus or transmit execution result information to an external apparatus.

4. The control apparatus according to claim 1,
    wherein, if the wireless communication circuit is to receive an image and the wireless communication circuit is transmitting the image stored in the memory, the controller causes the wireless communication circuit to stop transmitting the image.

5. The control apparatus according to claim 4,
    wherein, after the wireless communication circuit stops transmitting the image, the controller causes the wireless communication circuit to begin to receive an image from the imaging device.

6. The control apparatus according to claim 1,
    wherein the imaging device is an imaging device that detects X-rays and obtains an X-ray image, and
    wherein, if the sensor enters an accumulation state, the X-rays are radiated, or the sensor completes a detection of the X-rays, the controller limits the transmission of the image stored in the memory to the external image storage apparatus.

7. The control apparatus according to claim 1,
    wherein, if an imaging condition used for imaging is selected, the controller limits the transmission of the image stored in the memory to the external image storage apparatus.

8. The control apparatus according to claim 7,
wherein, if selection of an imaging condition used for imaging is canceled, the controller removes transmission limitations of the image stored in the memory to the external image storage apparatus.

9. The control apparatus according to claim 1,
wherein, if a plurality of images obtained by the imaging device are stored in the memory, the controller controls order of transmission of the plurality of images based on whether second identification information is associated with each of the plurality of images.

10. The control apparatus according to claim 1,
wherein the controller limits reception by the wireless communication circuit of the image from the imaging device while the wireless communication circuit is transmitting the image stored in the memory to the external image storage apparatus.

11. The control apparatus according to claim 1, further comprising:
a display controller configured to display, on a display unit, an imaging screen for performing imaging on the subject if a first operation, which is used for starting an examination including at least one imaging operation for the subject, is input,
wherein the examination information includes information about the subject, imaging protocol ID, and the information about the examination state,
wherein the information about the subject includes at least one of subject ID and a subject name,
wherein the imaging protocol is information including processing conditions about imaging,
wherein the imaging protocol ID is identification information about an imaging protocol,
wherein the information about the examination state includes an item for managing whether the examination has not been conducted, has been started, or has been completed,
wherein the information about the examination state is changed, if the first operation is input, and
wherein the examination is to be started if the information about the examination state indicating that the examination has not been conducted is changed to the information about the examination state indicating that the examination has been started.

12. The control apparatus according to claim 11, wherein the controller is configured to cause the display unit to display the imaging screen including an icon for receiving a second operation, which is used for ending an examination, and
wherein, if the second operation is input, the controller removes the limitation of the transmission of the image stored in the memory to the external image storage apparatus.

13. The control apparatus according to claim 1,
wherein the wireless communication circuit includes a single wireless communication module that is used to communicate with the imaging device and the external image storage apparatus.

14. The control apparatus according to claim 1,
wherein the wireless communication circuit communicates with the external image storage apparatus as a remote station and communicates with the imaging device operating as a remote station as a master station.

15. An X-ray imaging system comprising:
an imaging device configured to obtain an image using a sensor with a plurality of pixels arranged in two dimensions; and
the controller according to claim 1.

16. A method for controlling an imaging device that obtains an image using a sensor with a plurality of pixels arranged in two dimensions, the method comprising the steps of:
wirelessly receiving an image from the imaging device;
storing an image based on the received image in a memory;
starting an examination including at least one imaging operation for a subject if information about an examination state included in examination information obtained by receiving information from the external apparatus is changed, the examination information including the information about the examination state, the information about the examination state being information for managing a state of the examination including at least one imaging operation for the subject, and the external apparatus being different from the imaging device; and
limiting transmission of the stored image to an external image storage apparatus if the information about the examination state is changed.

17. A non-transitory computer-readable memory storing a program for causing a computer to implement the method according to claim 16.

18. A control apparatus that controls an imaging device that obtains an image using a sensor with a plurality of pixels arranged in two dimensions, the control apparatus comprising:
a wireless communication circuit configured to communicate with the imaging device and an external image storage apparatus;
a memory configured to store an image based on an image transmitted from the imaging device and received by the wireless communication circuit; and
a controller configured to limit transmission of the image stored in the memory to the external image storage apparatus,
wherein the controller starts limiting the transmission of the image stored in the memory to the external image storage apparatus if an imaging protocol that is information including processing conditions about imaging is selected by receiving information from an external apparatus, and the controller removes transmission limitations of the image stored in the memory to the external image storage apparatus if the selection of the imaging protocol is canceled by receiving information from the external apparatus, the external apparatus being different from the imaging device.

19. An X-ray imaging system comprising:
an imaging device configured to obtain an image using a sensor with a plurality of pixels arranged in two dimensions; and
the control apparatus according to claim 18.

20. A method for controlling an imaging device that obtains an image using a sensor with a plurality of pixels arranged in two dimensions, the method comprising:
wirelessly receiving an image from the imaging device;
storing an image based on the received image in a memory; and
limiting transmission of the stored image to an external image storage apparatus,
wherein in the limiting, transmission limitations of the stored image to the external image storage apparatus are started if an imaging protocol that is information including processing conditions about imaging is selected by receiving information from an external apparatus, and transmission limitations of the stored image to the external image storage apparatus are removed if the selection of the imaging protocol is canceled by receiving information from the external apparatus, the external apparatus being different from the imaging device.

21. A non-transitory computer-readable memory storing a program for causing a computer to implement the method according to claim 20.

* * * * *